(12) United States Patent
Hibner et al.

(10) Patent No.: US 12,733,974 B2
(45) **Date of Patent: *Sep. 15, 2026**

(54) CIRCULARITY SYSTEMS AND METHODS FOR VESSEL SEALERS

(71) Applicant: Cilag GmbH International, Zug (CH)

(72) Inventors: John A. Hibner, Mason, OH (US); Mark A. Davison, Maineville, OH (US); Tom Remm, Cincinnati, OH (US); Konstantin Zabotkin, Mason, OH (US)

(73) Assignee: Cilag GmbH International, Zug (CH)

( * ) Notice: Subject to any disclaimer, the term of this patent is extended or adjusted under 35 U.S.C. 154(b) by 344 days.

This patent is subject to a terminal disclaimer.

(21) Appl. No.: 18/326,594

(22) Filed: May 31, 2023

(65) Prior Publication Data

US 2024/0398467 A1 Dec. 5, 2024

(51) Int. Cl.
*A61B 18/14* (2006.01)
*A61B 17/00* (2006.01)
(Continued)

(52) U.S. Cl.
CPC .......... *A61B 18/1445* (2013.01); *A61B 34/71* (2016.02); *A61B 2017/0023* (2013.01);
(Continued)

(58) Field of Classification Search
CPC ........ A61B 18/1445; A61B 2017/0023; A61B 2017/00473; A61B 2017/00477;
(Continued)

(56) References Cited

U.S. PATENT DOCUMENTS

| | | | |
|---|---|---|---|
| 12,533,204 | B2 | 1/2026 | Hibner et al. |
| 2002/0188293 | A1 | 12/2002 | Manzo |

(Continued)

FOREIGN PATENT DOCUMENTS

| | | | |
|---|---|---|---|
| EP | 3473201 | A1 | 4/2019 |
| WO | 2014004251 | A2 | 1/2014 |
| WO | 2015023865 | A1 | 2/2015 |

OTHER PUBLICATIONS

International Search Report and Written Opinion received for PCT Application No. PCT/IB2024/055283, 15 pages, mailed on Sep. 19, 2024.

*Primary Examiner* — Khadijeh A Vahdat

(74) *Attorney, Agent, or Firm* — Vorys, Sater, Seymour and Pease LLP

(57) ABSTRACT

A method of replacing a consumable of a surgical tool includes securing the surgical tool, which includes a drive housing, an elongate shaft extending distally from the drive housing, an end effector arranged at a distal end of the shaft, and a wrist interposing the distal end of the shaft and the end effector. The method further includes moving the elongate shaft proximally and thereby exposing internal portions of the wrist and the end effector, moving the end effector distally to separate the end effector from the wrist, disconnecting the end effector from proximal portions of the surgical tool, replacing the consumable of the surgical tool, reconnecting the end effector to the proximal portions of the surgical tool, moving the end effector proximally to re-attach the end effector to the wrist, and moving the shaft distally to occlude the internal portions of the wrist and the end effector.

16 Claims, 19 Drawing Sheets

(51) Int. Cl.
*A61B 34/00* (2016.01)
*A61B 18/00* (2006.01)
*A61B 34/30* (2016.01)

(52) U.S. Cl.
CPC ............... *A61B 2017/00473* (2013.01); *A61B 2017/00526* (2013.01); *A61B 2018/00428* (2013.01); *A61B 2018/0063* (2013.01); *A61B 2018/1455* (2013.01); *A61B 2034/302* (2016.02); *A61B 2034/305* (2016.02)

(58) Field of Classification Search
CPC ........... A61B 2017/00526; A61B 2018/00172; A61B 2018/00428; A61B 2018/0063; A61B 2018/1455; A61B 2018/1495; A61B 2034/302; A61B 2034/305; A61B 34/71; A61B 2090/0806; A61B 2090/0813
See application file for complete search history.

(56) References Cited

U.S. PATENT DOCUMENTS

2003/0109877 A1 6/2003 Morley et al.
2007/0123855 A1* 5/2007 Morley .................. A61B 34/71 606/50
2013/0041292 A1 2/2013 Cunningham
2013/0085516 A1* 4/2013 Kerr ..................... A61B 17/282 606/167
2017/0181789 A1* 6/2017 Ding .................. A61B 18/1445
2018/0132887 A1* 5/2018 Asher ................ A61B 18/1445

* cited by examiner 200
202
1302b
1304
615
1302a
612a
210
614a 202
1306
615
612a
612b 2208
2206

2204
2202
2200

CIRCULARITY SYSTEMS AND METHODS FOR VESSEL SEALERS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

MIS instruments incorporate various high-wear components that, over time, can mechanically or physically degrade and thereby limit the useful life of the instrument. Consequently, most MIS instruments are designed to be used only for a predetermined number a procedures, following which the instrument is often discarded. As can be appreciated, this can have an adverse impact on the environment.

In an effort to maintain the value of products, while simultaneously not creating additional environmental waste, companies and manufacturers are progressively looking for ways to incorporate "circularity" into their business model. Circularity is an economic model that follows the three "Rs": reuse, reprocess, and recycle, and aims to retain the lifespan of products through repair and maintenance, reusing, remanufacturing, or upcycling.

What is needed is a process or methodology of circularity concerning the reuse and recycling of MIS instruments, which minimizes the impact on the environment.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical tools and, more particularly, to prolonging the lifespan of surgical tools by implementing circularity systems and methods that result in replacement of one or more consumables included in the surgical tool.

The utilization or "lifespan" of a majority of robotic (and non-robotic) surgical tools is often limited due to the life or durability of just a few components within the surgical tool, referred to herein as "consumables". Embodiments disclosed herein describe how the design of the surgical tool can be modified to enable the consumable to be replaced rather easily, without requiring the surgical tool to be completely disassembled. Accordingly, the embodiments disclosed herein may prove advantageous in mitigating or entirely eliminating the need to scrap an entire surgical tool, but instead rehabilitate the used surgical tool by replacing one or more consumables.

Figure 1:
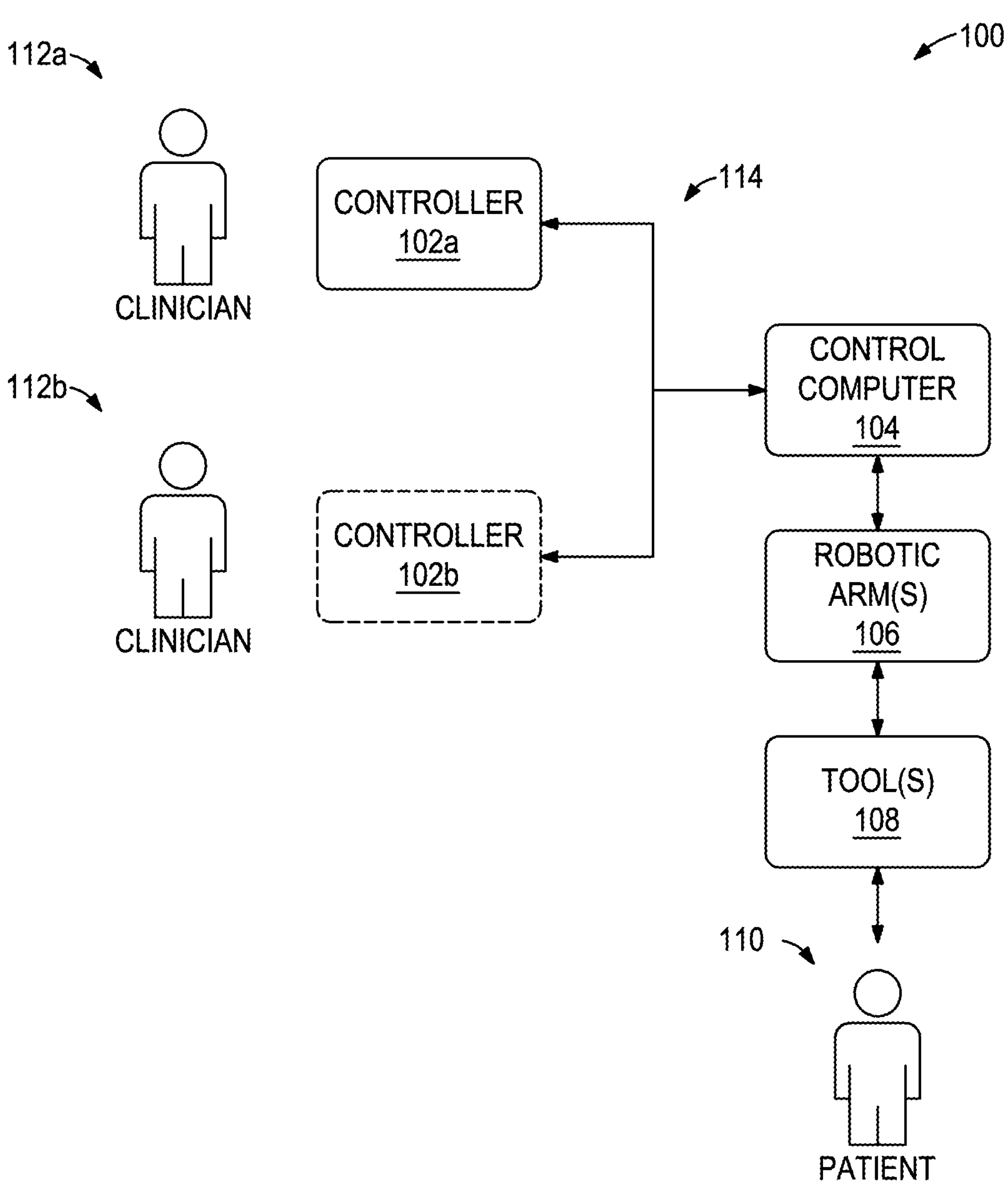
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
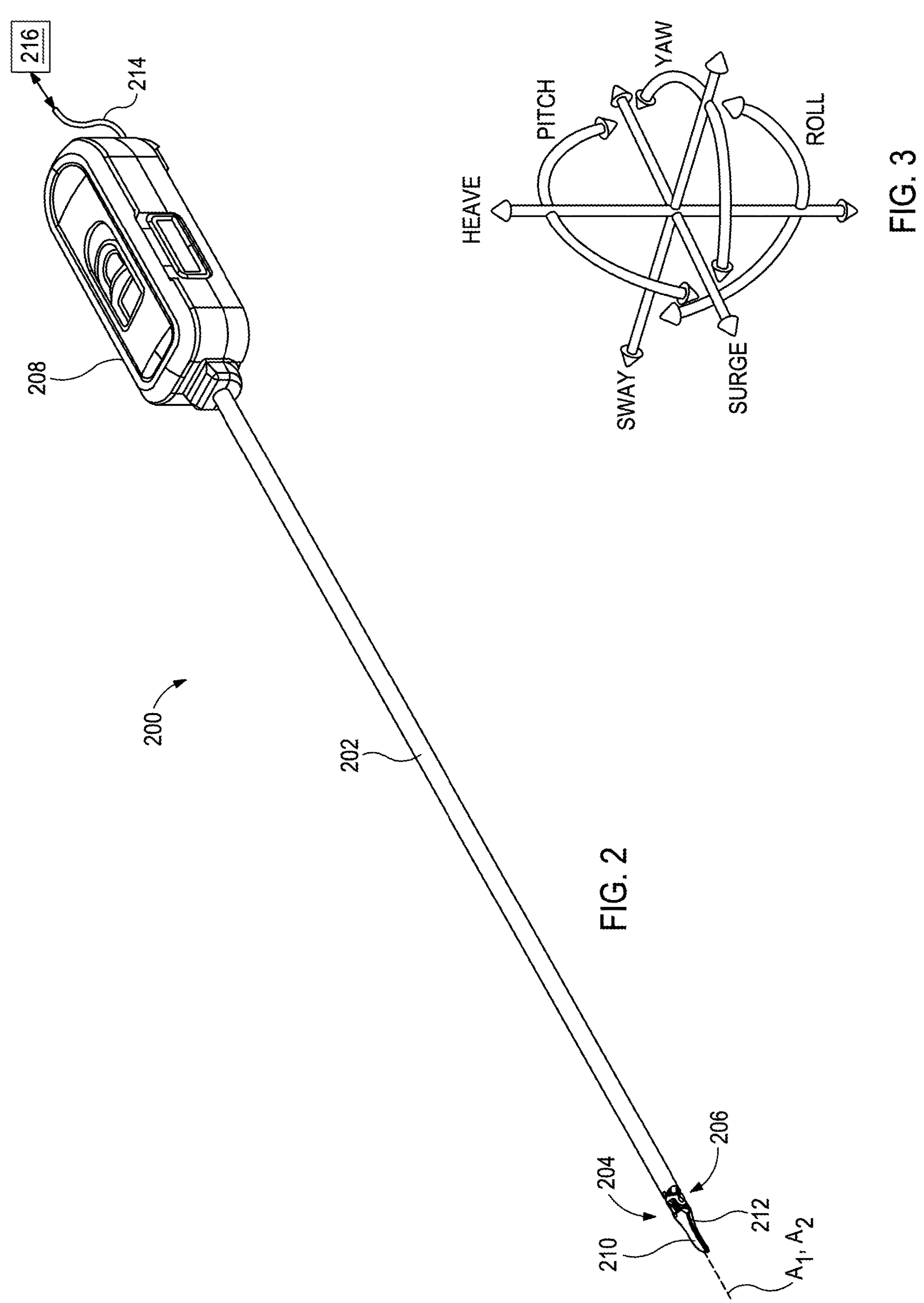
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

Similar to most surgical tools, the surgical tool 200 includes various high-wear components referred to herein as "consumables" that, over time, can mechanically or physically degrade and thereby limit the useful life of the surgical tool 200. Consequently, the surgical tool 200 may be designed to be used for only a predetermined number of procedures. Once the predetermined number of procedures is reached, the operator (e.g., a nurse, a doctor, etc.) may be unable to continue using the surgical tool 200. In such cases, the surgical tool 200 would conventionally be discarded, which can have an adverse impact on the environment.

According to embodiments of the present disclosure, instead of discarding the surgical tool 200, the surgical tool 200 may be subject to circularity processing or a circular economy model or approach designed to reprocess and recycle the surgical tool 200 for further use. In circularity processing, the surgical tool 200 is decommissioned upon reaching the predetermined number of procedures, and then subsequently sent to a service center where trained technicians clean and mount the surgical tool 200 to a disassembly fixture. While mounted to the disassembly fixture, various portions of the surgical tool 200 may be disassembled to access and remove one or more consumables that form part of the surgical tool 200. The removed consumables can then be cleaned and refurbished or replaced with new consumables. The surgical tool 200 may then be reassembled, tested, delivered to a distribution center, and subsequently sent to an end user (e.g., a hospital, a surgeon, an operator, etc.) for further use.

Figure 4:
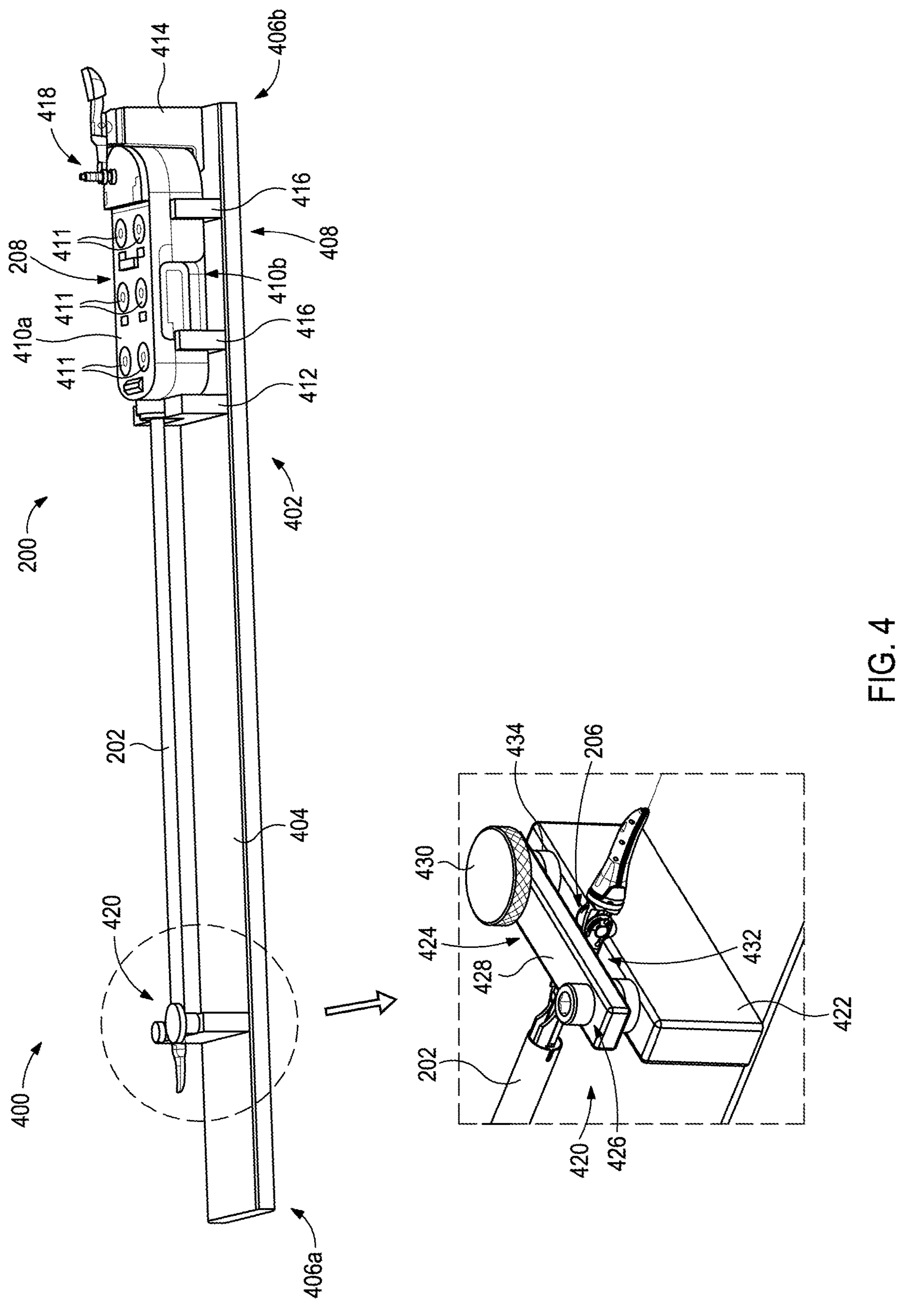
FIG. 4 is an isometric side view of an example circularity processing system, according to one or more embodiments.

FIG. 4 is an isometric side view of an example surgical tool circularity processing system 400, according to one or more embodiments. As illustrated, the surgical tool circularity processing system 400 includes a disassembly fixture 402 configured to receive and mount the surgical tool 200. The disassembly fixture 402 may be provided at a service center that employs technicians trained to clean, disassemble, and refurbish the surgical tool 200, as described herein.

As illustrated, the disassembly fixture 402 provides an elongate base 404 having a first or "distal" end 406*a* and a second or "proximal" end 406*b* opposite the distal end 406*a*. In some embodiments, as illustrated, the base 404 may exhibit a generally rectangular shape, but could alternatively exhibit other shapes without departing from the scope of the disclosure.

A drive housing mount 408 may be provided and otherwise defined at the proximal end 406*b* and configured to receive and seat the drive housing 208, which may include a bottom portion 410*a* mateable with a top portion 410*b*. In the illustrated embodiment, the drive housing 208 is shown received within the drive housing mount 408 such that the bottom portion 410*a* faces upwards and is otherwise exposed. In such embodiments, some or all of the bottom portion 410*a* may be removed by the technician to access various internal components of the drive housing 208, as described in more detail below. Moreover, in such embodiments, a robotic manipulator (not shown) may be attached to the bottom portion 410*a* to operate the exposed drive inputs 411 of the drive housing 208. In other embodiments, however, the drive housing 208 may be received within the drive housing mount 408 with the top portion 410*b* facing upwards, without departing from the scope of the disclosure.

As illustrated, the drive housing mount 408 may include a plurality of structural elements extending from or otherwise forming part of the body 404 and designed to receive and seat the drive housing 208. More particularly, the drive housing mount 408 may include a cradle or "yoke" 412, a rear support 414, and one or more side supports 416 (two visible) provided at various locations between the yoke 412 and the rear support 414. The yoke 412 may be configured to support the distal end of the drive housing 208, and the rear support 414 may be configured to support the proximal end of the drive housing 208. The side supports 416 may be configured to support the lateral sides of the drive housing 208.

In some embodiments, the drive housing mount 408 may further include a clamp 418 operable to secure the drive housing 208 to the base 404 when properly received within the drive housing mount 408. In some embodiments, as illustrated, the clamp 418 may be mounted to the rear support 414, but could alternatively be mounted other portions of the drive housing mount 408 or the base 404, without departing from the scope of the disclosure.

A vice, referred to herein as an end effector mount 420, may be provided and otherwise defined at or near the distal end 406*a* of the base 404 and configured to receive and seat the distal end of the surgical tool 200. More specifically, and as shown in the enlarged, inset graphic, the end effector mount 420 may include a bracket or stand 422 and a securing clasp or mechanism 424 pivotably attached to the stand 422. The securing mechanism 424 may include a pivot joint 426, a securing bar 428 extending from the pivot joint 426, and a mechanical fastener 430 arranged at the end of the securing bar 428 opposite the pivot joint 426. As mounted to the pivot joint 426, the securing bar 428 may be vertically offset a short distance from the stand 422, such that a gap 432 is provided between the securing bar 428 and the top of the stand 422. The gap 432 may be large enough to receive the distal end of the surgical tool 200 when the securing mechanism 424 is secured to the stand 422.

To secure the distal end of the surgical tool 200 to the disassembly fixture 402 and, more particularly, to the end effector mount 420, the distal end of the surgical tool 200 is first placed atop the stand 422 such that the shaft 202 or portions of the wrist 206 engage the top of the stand 422. The securing bar 428 may then be pivoted about the pivot joint 426 until the mechanical fastener 430 is able to locate and mate with a corresponding securing receptor 434. Operating or otherwise securing the mechanical fastener 430 to the securing receptor 434 may place a load on the distal end of the surgical tool 200, which helps prevent the surgical tool 200 from moving up or down, or translating axially. In the illustrated embodiment, the mechanical fastener 430 comprises a thumbscrew, but could alternatively comprise other types of mechanical fasteners or fastening means suitable for securing the securing bar 428 to the stand 422 and thereby helping to secure the surgical tool 200 to the disassembly fixture 402.

Those skilled in the art will readily appreciate that the end effector mount 420 and the securing mechanism 424 are merely one example embodiment consistent with the principles of the present disclosure. Indeed, other means and configurations of the end effector mount 420 and/or the securing mechanism 424 are possible and contemplated herein, without departing from the scope of the disclosure.

Figure 5A:
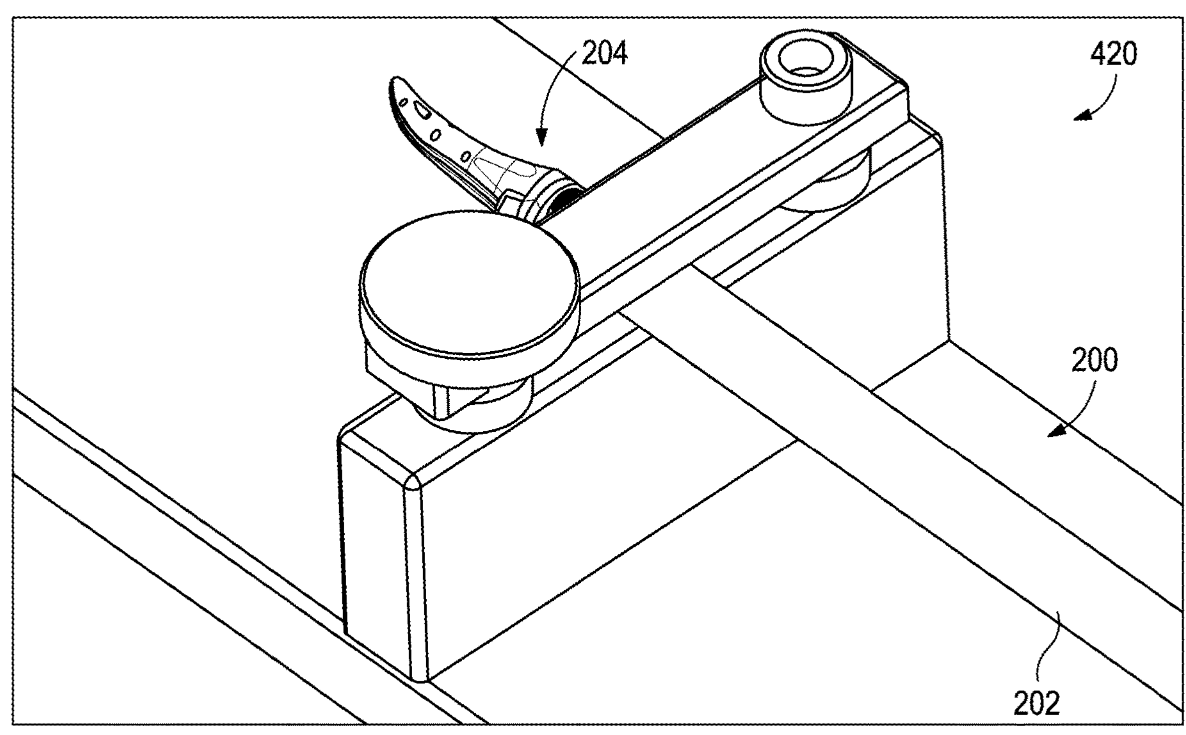
FIGS. 5A and 5B are enlarged isometric views of the distal end of the surgical tool of FIG. 2 as mounted to the end effector mount of FIG. 4.
Figure 5B:
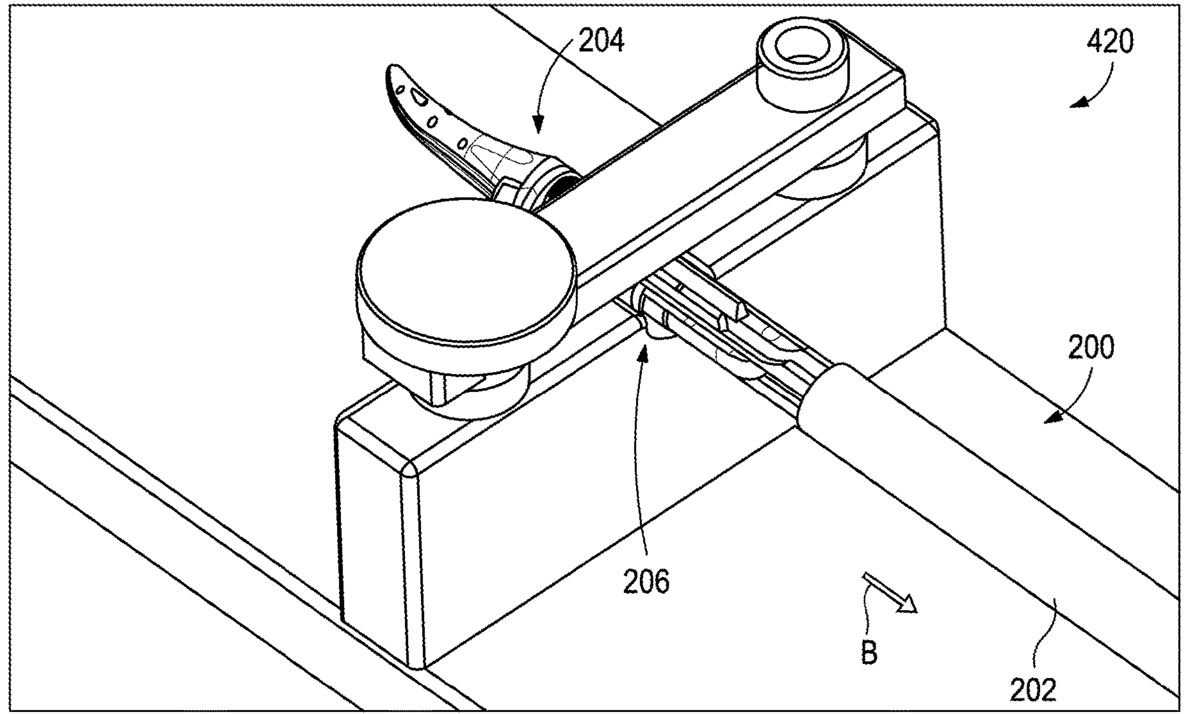

FIGS. 5A and 5B are enlarged isometric views of the distal end of the surgical tool 200 mounted to the end effector mount 420, according to one or more embodiments. Once the distal end of the surgical tool 200 is properly mounted to the end effector mount 420, as shown in FIG. 5A, the shaft 202 may be moved and otherwise translated proximally relative to the end effector 204, as indicated by the arrow B in FIG. 5B. In some embodiments, as described below, it may be necessary to release the proximal end of the shaft 202 within the drive housing 208 (FIGS. 2 and 4) prior to moving the shaft 202 proximally. Once the proximal end of the shaft 202 is released, however, the shaft 202 may be manually translated in the proximal direction B, which exposes internal portions of the end effector 204 and the wrist 206.

Figure 6A:
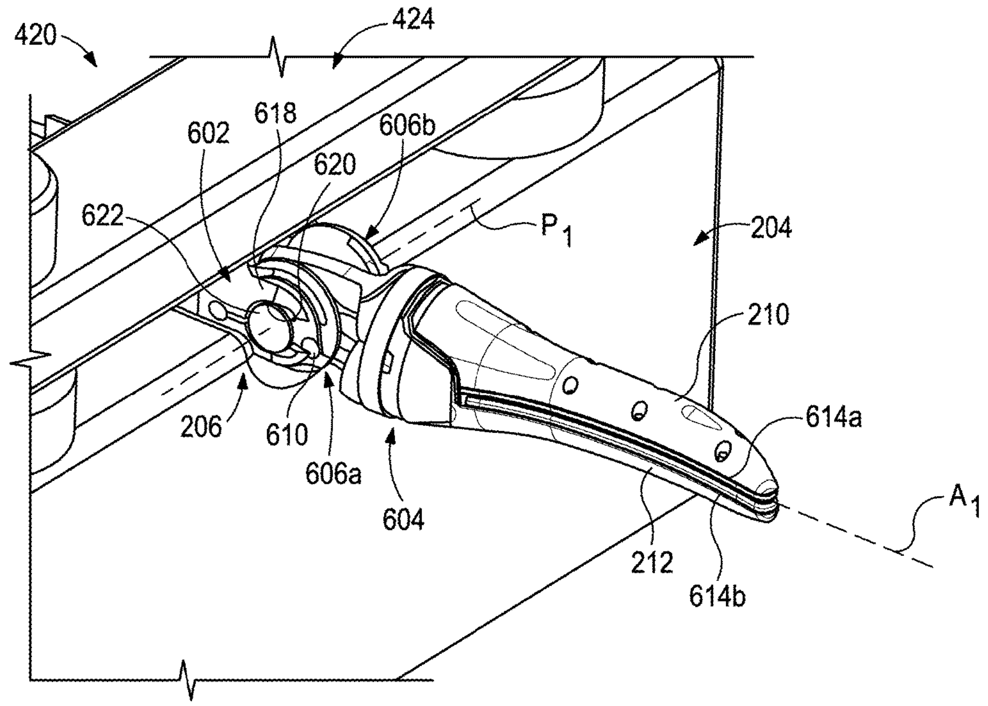
FIGS. 6A and 6B are enlarged isometric views of the distal end of the end effector of FIG. 2 mounted to the end effector mount of FIG. 4, according to one or more embodiments.
Figure 6B:
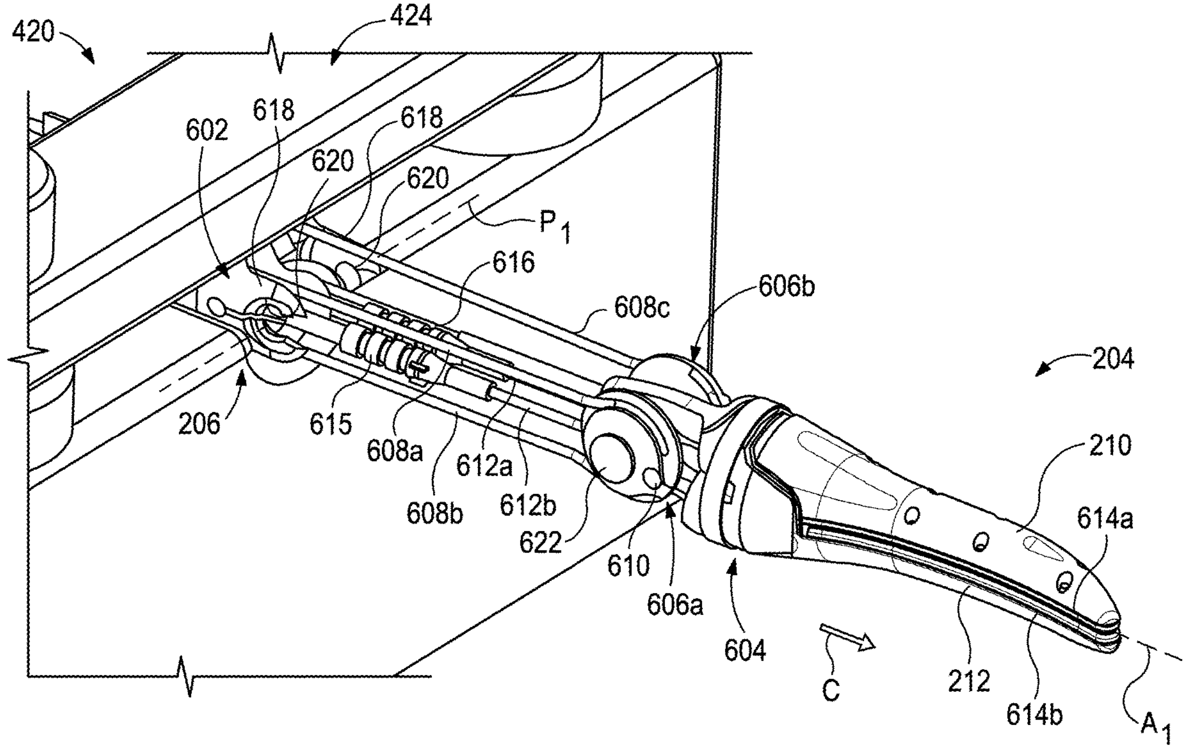

FIGS. 6A and 6B are enlarged isometric views of the distal end of the end effector 204 mounted to the end effector mount 420, according to one or more embodiments. In the illustrated embodiment, the securing mechanism 424 is clamped down against a portion of the wrist 206, which interposes the end effector 204 and the shaft 202 (FIGS. 2, 4, and 5A-5B). As illustrated, the wrist 206 may include at least a distal clevis 602, which may help facilitate articulation of the wrist 206 relative to the shaft 202. In the illustrated depiction, the securing mechanism 424 is clamped down against the distal clevis 602 to secure the end effector 204 to the end effector mount 420. In other embodiments, however, the securing mechanism 424 may be clamped down against other portions of the wrist 206 to secure the end effector 204 to the end effector mount 420.

In some embodiments, the wrist 206 may further include a linkage 604 arranged distal to the distal clevis 602 and operatively mounted to the jaws 210, 212. First and second pulleys 606*a* and 606*b* may be rotatably mounted to the distal end of the distal clevis 602 at a pivot axis $P_1$ of the wrist 206. The linkage 604 may be arranged distal to the pivot axis $P_1$ and operatively mounted to the jaws 210, 212, and the pivot axis $P_1$ is substantially perpendicular (orthogonal) to the longitudinal axis $A_1$ of the end effector 204. As discussed below, the linkage 604 may comprise two or more matable parts, and may be operable to help hold the jaws 210, 212 together.

As best seen in FIG. 6B, a plurality of drive cables, shown as drive cables 608*a*, 608*b*, 608*c*, and 608*d* (occluded), extend proximally from the end effector 204 and extend at least partially through the wrist 206. The drive cables 608*a-d* may form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 608*a-d* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 608*a-d* are depicted in FIG. 6B, more or less than four may be employed, without departing from the scope of the disclosure.

The drive cables 608*a-d* extend from the end effector 204 toward the drive housing 208 (FIGS. 2 and 4) where they are operatively coupled to various actuation mechanisms or devices that facilitate longitudinal movement (translation) of the drive cables 608*a-d*. Selective actuation of the drive cables 608*a-d* at the drive housing 208 applies tension (i.e., pull force) to the given drive cable 608*a-d* in the proximal direction, which urges the given drive cable 608*a-d* to translate longitudinally.

The distal end of each drive cable 608*a-d* may terminate at the first or second pulleys 606*a,b*, thus operatively coupling each drive cable 608*a-d* to the end effector 204. In the illustrated embodiment, the distal ends of the first and second drive cables 608*a,b* may be coupled to each other and terminate at the first pulley 606*a*, and the distal ends of the third and fourth drive cables 608*c,d* may be coupled to each other and terminate at the second pulley 606*b*. In at least one embodiment, the distal ends of the first and second drive cables 608*a,b* and the distal ends of the third and fourth drive cables 608*c,d* may each be coupled together at corresponding ball crimps 610 (one visible) mounted to the first and second pulleys 606*a,b*, respectively.

As also best seen in FIG. 6B, in some embodiments, first and second electrical conductors 612*a* and 612*b* extend longitudinally through the wrist 206 and terminate at the end effector 204 to supply electrical energy thereto. More particularly, the first electrical conductor 612*a* terminates at a first or "upper" electrode 614*a* secured to the upper jaw 210, and the second electrical conductor 612*b* terminates at a second or "lower" electrode 614*b* secured to the lower jaw 212. When the jaws 210, 212 are closed, the electrodes 614*a,b* face (oppose) each other.

In some embodiments, the electrical conductors 612*a,b* may each comprise a wire, but may alternatively comprise a rigid or semi-rigid shaft, rod, or strip (ribbon) made of a conductive material. The electrical conductors 612*a,b* may be partially covered with an insulative covering (overmold) made of a non-conductive material. Routing the electrical conductors 612*a,b* to the corresponding electrodes 614*a,b*, respectively, allows the end effector 204 to operate in bipolar RF operation. In other embodiments, however, only one electrode 614*a,b* may be included and the end effector 204 and the opposing jaw acts as the other electrode while operating in bipolar RF operation.

In some embodiments, as illustrated, each electrical conductor 612*a,b* may include a corresponding electrical connector 615 configured to join two opposing lengths of the electrical conductors 612*a,b*. The distal lengths of the electrical conductors 612*a,b* extend to the electrodes 614*a,b*, while the proximal lengths (not shown) of the electrical conductors 614*a,b* extend to the drive housing 208 (FIGS. 2 and 4). The electrical connectors 615 allow the distal lengths of the electrical conductors 612*a,b* to be detached from the proximal lengths when the end effector 204 is removed, as described below.

As mentioned above, the end effector 204 comprises a combination tissue grasper and vessel sealer, and may further include a knife (not shown), alternately referred to as a "cutting element" or "blade." As described in more detail below, the knife is aligned with and configured to traverse a guide track (not shown) defined longitudinally in one or both of the upper and lower jaws 210, 212. The knife may be operatively coupled to the distal end of a drive rod 616 (FIG. 6B) that extends longitudinally and passes through the wrist 206. Longitudinal movement (translation) of the drive rod 616 correspondingly moves the knife within the guide track(s). Similar to the drive cables 608*a-d*, the drive rod 616 may form part of the actuation systems housed within the drive housing 208 (FIG. 2). Selective actuation of a corresponding drive input will cause the drive rod 616 to move distally or proximally, and correspondingly move the knife in the same longitudinal direction.

The distal clevis 602 provides opposing first and second arms 618 (only one visible in FIG. 6A) laterally offset from each other and extending distally toward the end effector 204. A gap (space) is formed between the arms 618 to receive the pulleys 606*a,b* and also provide space to accommodate the other elements of the end effector 204 that pass through the wrist 206 and extend to the end effector 204. In some embodiments, as illustrated, each arm 618 may provide and otherwise define an open-ended slot 620 (only one visible in FIG. 6A) open in the distal direction and configured to receive and seat a corresponding retaining cap or "end cap" 622 (only one visible) pertaining to each pulley 606*a,b*. In some embodiments, the end caps 622 may form an integral part of the corresponding pulley 606*a,b*. In other embodiments, however, the end caps 622 may each comprise separate component parts configured to be operatively coupled to the pulleys 606*a,b* and configured to help secure the pulleys 606*a,b* to the distal clevis 602.

As indicated above, each slot 620 is open-ended in the distal direction. Consequently, the end caps 622 may be detached from the distal clevis 602 by pulling the end effector 204 in the distal direction, as shown by the arrow C, and thereby separating the end caps 622 from the distal clevis 612. FIG. 6A depicts the end effector 204 in a first or "assembled" state, and FIG. 6B depicts the end effector 204 in a second or "extended" state, where the end effector 204 is manually moved in the distal direction C to separate the pulleys 606*a,b* from the corresponding open-ended slots 620. To enable the end effector 204 to be pulled distally, the surgical tool 200 (FIG. 2) may provide or otherwise incorporate slack into the design at the drive housing 208 (FIGS. 2 and 4). In such embodiments, for example, the drive cables 608*a-c*, the electrical conductors 612*a,b*, and the drive rod 616 may each be configured to payout slack as the end effector 204 is pulled distally in the direction C. In at least one embodiment, this can be accomplished for the drive cables 608*a-d* by rotating the input capstans to unspool or payout cable through various spooling capstan mechanisms. Whereas the electrical conductors 612*a,b* and the drive rod 616 may each be disconnected prior to (or after) extending the end effector 204 distally, as generally described below.

Figure 7A:
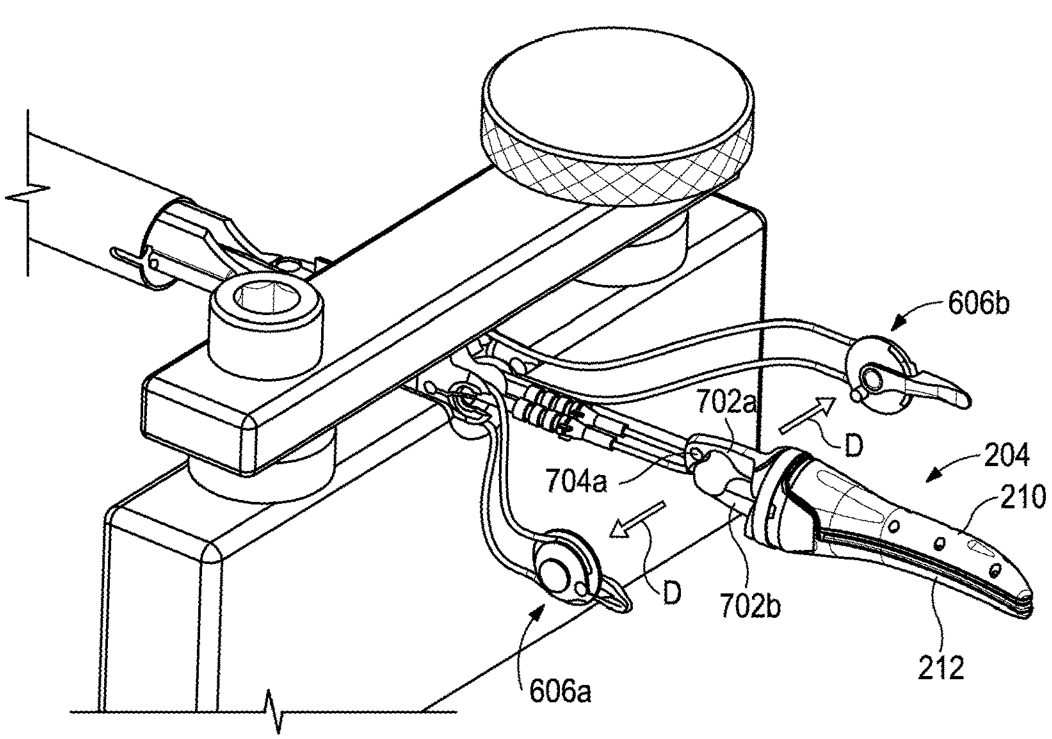
FIG. 7A depicts the end effector in an additional step of disassembly, according to one or more embodiments of the present disclosure.

FIG. 7A depicts the end effector 204 in an additional step of disassembly, according to one or more embodiments of the present disclosure. Once the end effector 204 is extended distally, as described above, the pulleys 606*a,b* may be separated or exploded laterally from the end effector 204, as shown by the arrows D.

More particularly, the first jaw 210 provides a first jaw extension 702*a* and the second jaw 212 provides a second jaw extension 702*b*, and each jaw extension 702*a,b* extends proximally from the corresponding jaw 210, 212. The first pulley 606*a* may be rotatably coupled to the first jaw extension 702*a* such that movement (rotation) of the first pulley 606*a* correspondingly moves (rotates) the first jaw 210, and the second pulley 606*b* may be rotatably coupled to the second jaw extension 702*b* such that movement (rotation) of the second pulley 606*b* correspondingly moves (rotates) the second jaw 212. The first pulley 606*a* provides a first jaw pin (not visible) configured to mate with a first jaw aperture 704*a* defined on the first jaw extension 702*a*, and the second pulley 606*b* may provide or define a second jaw pin 706 configured to mate with a second jaw aperture 704*b* (FIG. 7B) defined on the second jaw extension 702*b*. The jaw pins 706 are eccentric to the pivot axis, which allows the pulleys 606*a,b* to rotate to pivot the jaws 210, 212 between open and closed positions. With the pulleys 606*a,b* separated from the end effector 204, however, the pulleys 606*a,b* no longer constrain the assembly.

Figure 7B:
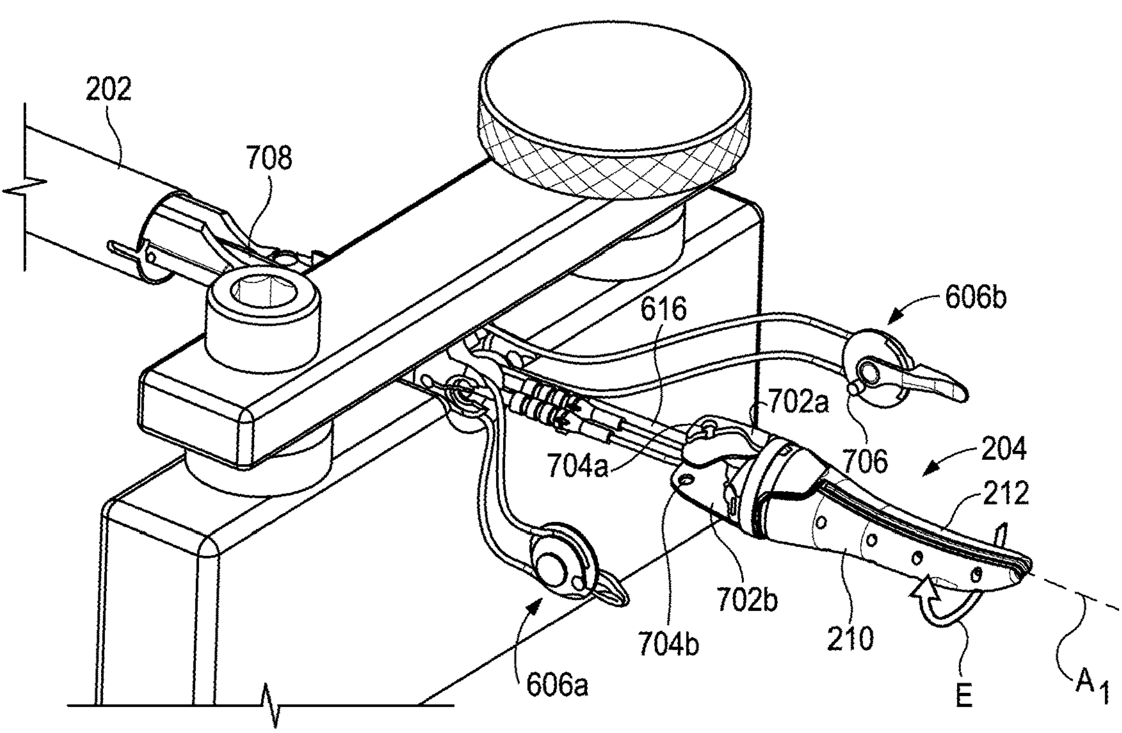
FIG. 7B depicts the end effector in an additional step of disassembly, according to one or more additional embodiments of the present disclosure.

FIG. 7B depicts the end effector 204 in an additional step of disassembly, according to one or more additional embodiments of the present disclosure. With the pulleys 606*a,b* separated laterally from the end effector 204, as generally described above with reference to FIG. 7A, the end effector 204 is now ready to be completely detached from the shaft 202 and its sub components. In at least one embodiment, the end effector 204 may be rotated about the longitudinal axis $A_1$ of the shaft 202 in an angular direction (e.g., clockwise), as shown by the arrow E. In some configurations, rotating the end effector 204 in the angular direction E will allow the drive rod 616 to mechanically detach from a push rod 708 (partially visible) extending within the shaft 202. The push rod 708 is a generally rigid rod that extends to the drive housing 208 (FIGS. 2 and 4) and may be operatively coupled to an actuation mechanism operable to axially translate the push rod 708 within the shaft 202, and actually translating the push rod 708 correspondingly acts on the drive rod 616 in the same direction.

Figure 8:
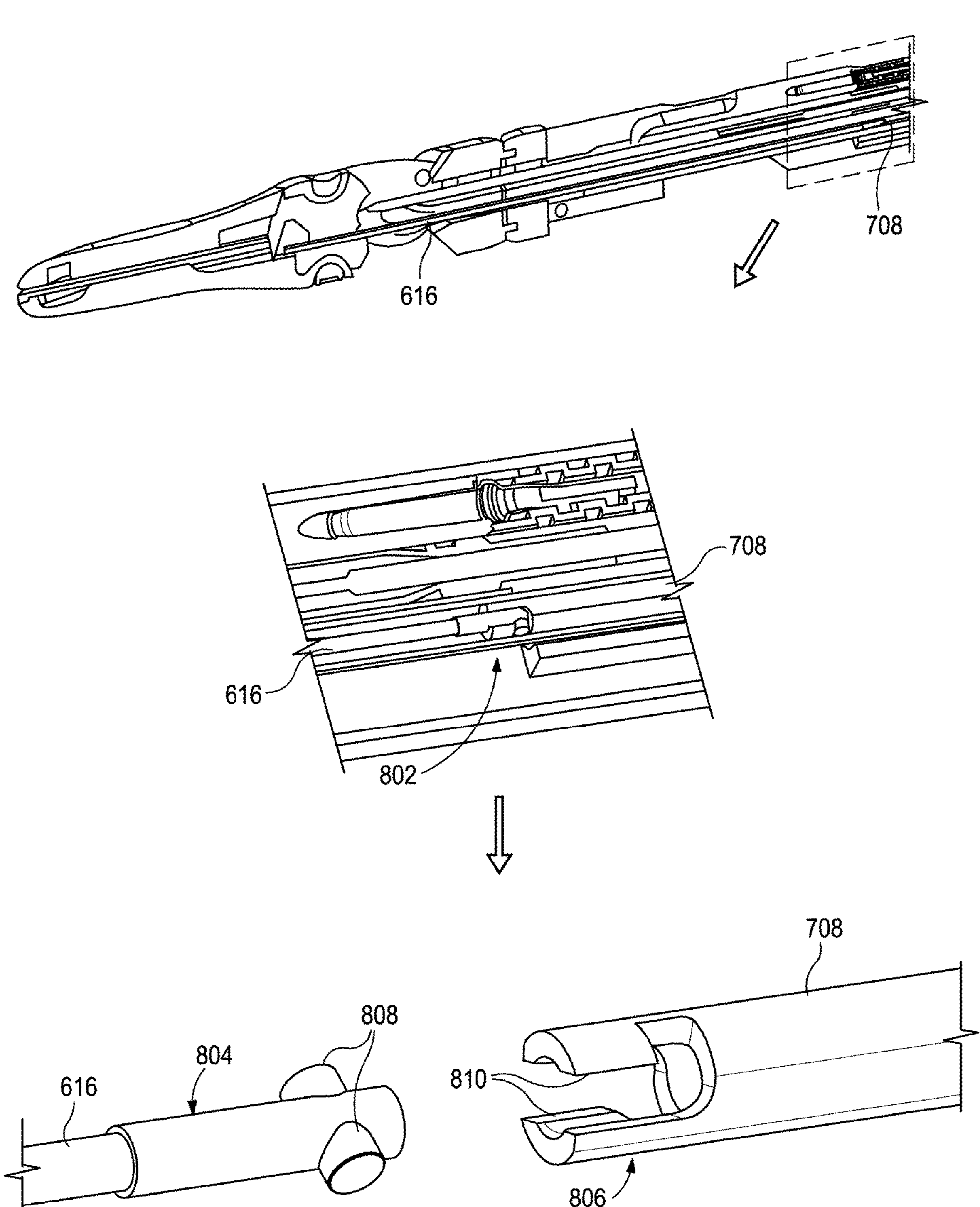
FIG. 8 are enlarged progressive views of the interconnection between the drive rod and the push rod, according to one or more embodiments.

FIG. 8 depicts enlarged, progressive views of the interconnection between the drive rod 616 and the push rod 708, according to one or more embodiments. As illustrated, the drive rod 616 may be operatively and releasably coupled to the push rod 708 at a releasable connection 802.

In at least one embodiment, the releasable connection 802 may comprise a bayonet-style connection. More specifically, the releasable connection 802 may include a bayonet connector 804 provided at the proximal end of the drive rod 616, and the distal end of the push rod 708 may comprise and otherwise define a female receptor 806. In some embodiments, however, the position of the bayonet connector 804 and the female receptor 806 may be switched. In such embodiments, the bayonet connector 804 may instead be provided at the distal end of the push rod 708, and the proximal end of the drive rod 616 may include the female receptor 806.

The bayonet connector 804 includes one or more radial pins 808 configured to be received within matching L-shaped slot(s) 810 defined in the female receptor 806. In such embodiments, rotating the end effector 204 (FIG. 7B) in the angular direction E (FIG. 7B) will allow the radial pins 808 to be released from the L-shaped slot(s) 810, thereafter moving the drive rod 616 and the distal direction C.

Figure 9:
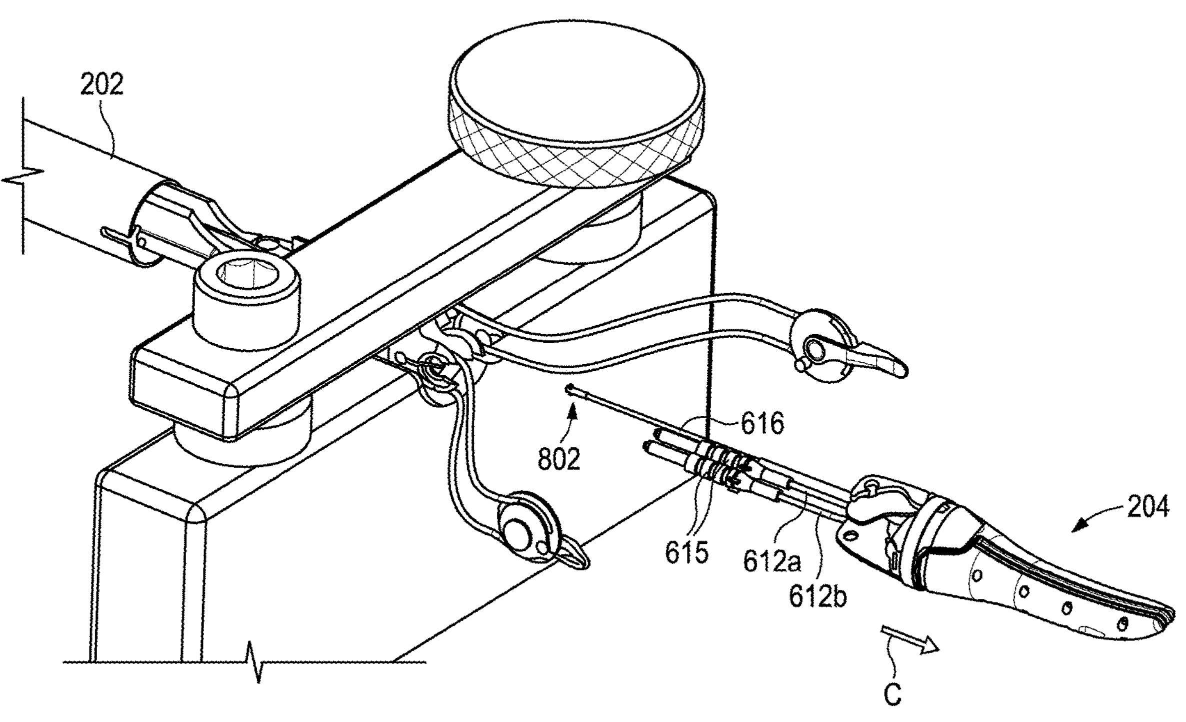
FIG. 9 depicts the end effector in an additional step of disassembly, according to one or more additional embodiments of the present disclosure.

FIG. 9 depicts the end effector 204 in an additional step of disassembly, according to one or more additional embodiments of the present disclosure. More specifically, once the releasable connection 802 of the drive rod 616 is disconnected, as generally described above, the end effector 204 may be manually translated in the distal direction C, thereby separating the end effector 204, the drive rod 616, and the electrical conductors 612*a,b* from the remaining (proximal) portions of the shaft 202 and its sub components.

As mentioned above, each electrical conductor 612*a,b* includes a corresponding electrical connector 615, and pulling the end effector 204 in the distal direction C causes the electrical connectors 615 to disengage from proximal lengths (not visible) of the electrical conductors 612*a,b*. In some embodiments, for example, each electrical connector 615 may comprise an interference fit plug, such as a banana style clip. In such embodiments, the electrical connectors 902 may be disconnected from corresponding connections within the shaft 202 by merely pulling in the distal direction C and thereby detaching the banana style clip.

Figure 10A:
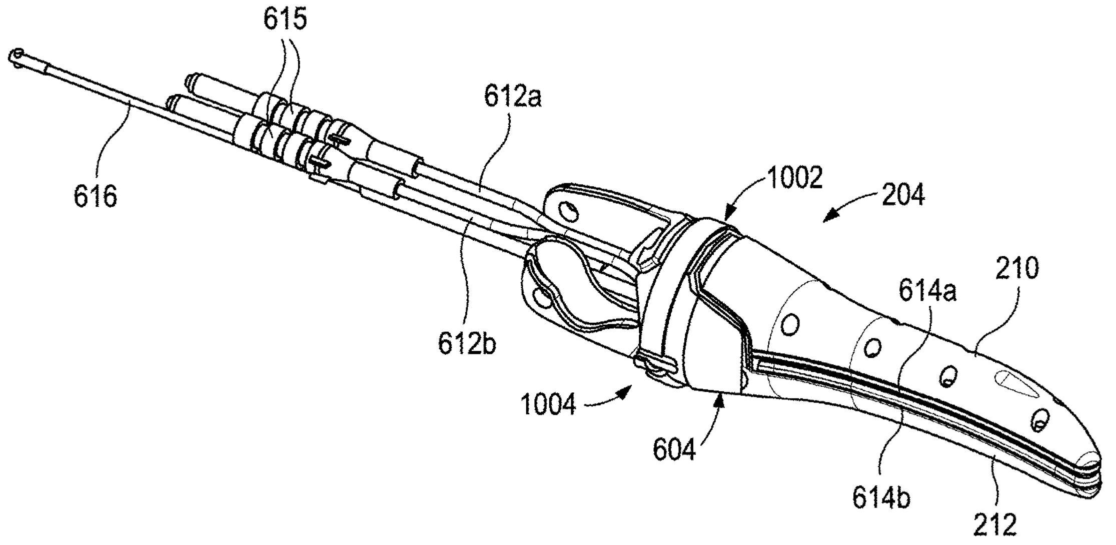
FIGS. 10A and 10B depict additional steps of disassembly of the end effector, according to one or more additional embodiments of the present disclosure.
Figure 10B:
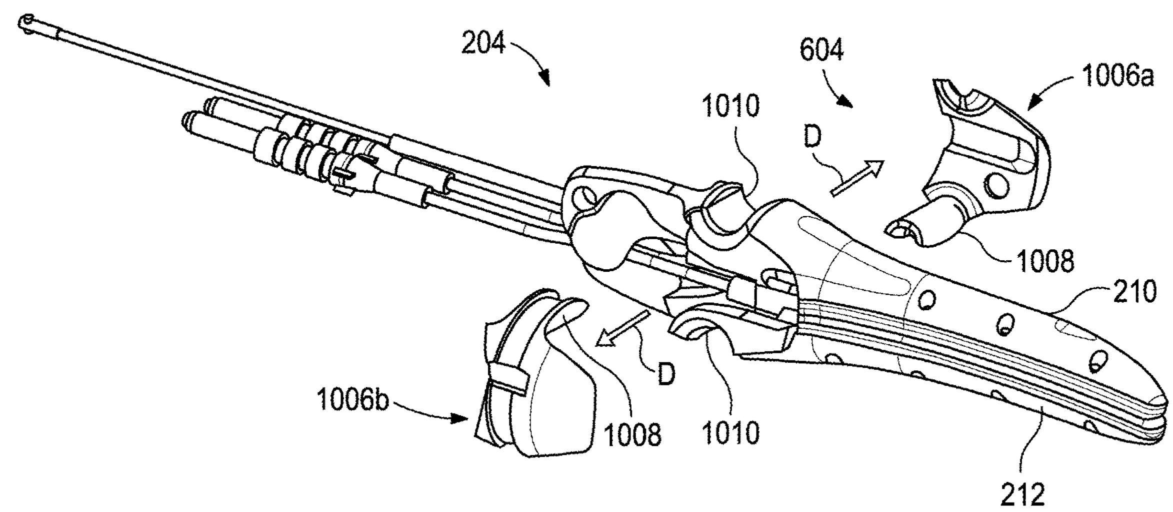

FIGS. 10A and 10B depict additional steps of disassembly of the end effector 204, according to one or more additional embodiments of the present disclosure. Referring first to FIG. 10A, if desired, the entire end effector 204, including all of the "consumables" or high-wear components pertaining to the end effector 204, may be replaced at this point. In such embodiments, new or refurbished end effector, electrical conductors and corresponding electrical connectors, drive rod, and knife may be provided, and the foregoing steps of disassembly and detachment up to this point may be reversed to reattach the component parts to the remaining (proximal) portions of the surgical tool 200 (FIG. 2).

Alternatively, if it is desired to replace individual "consumables" pertaining to the end effector 204, the end effector 204 may undergo further disassembly by detaching, decoupling, or otherwise breaking a securing band 1002 that extends about the linkage 604 and holds the jaws 210, 212 in place. The securing band 1002 may be made of a variety of materials including, but not limited to, a metal, a polymer, an elastomer, a composite material, and any combination thereof. In FIG. 10A, the securing band 1002 is shown having been cut or severed at a break or separation point 1004. In other embodiments, instead of being cut or severed, the securing band 1002 may be decoupled, such as by removing a mechanical fastener or a mechanical coupling.

Example "consumables" of the end effector 204 that may be replaced by further disassembling the end effector 204 include, but are not limited to, the jaws 210, 212 (one or both), the drive rod 616, a knife (not shown) secured to the distal end of the drive rod 616, the electrical conductors 612*a,b* and corresponding electrical connectors 615, and the electrodes 614*a,b* secured to the upper and lower jaws 210, 212, respectively.

Referring now to FIG. 10B, once the securing band 1002 (FIG. 10A) is removed, the linkage 604 may then be removed from the jaws 210, 212. In the illustrated embodiment, the linkage 604 includes two or more component parts that are joined or mated to help secure the jaws 210, 212. More particularly, the linkage 604 comprises opposing first and second linkage portions 1006*a,b*, and joining the linkage portions 1006*a,b* helps rotatably secure the jaws 210, 212. In disassembling the end effector 204, the linkage portions 1006*a,b* may be removed in the lateral direction, as shown by the arrows D.

As illustrated, each linkage portion 1006*a,b* may provide or define a lateral arm 1008, and each jaw 210, 212 defines a saddle or "groove" 1010 configured to receive a corresponding one of the lateral arms 1008, and thereby provide corresponding inner jaw pivot surfaces for the jaws 210, 212. In the illustrated embodiment, the lateral arm 1008 of the second linkage portion 1006*b* is received within the groove 1010 defined by the first jaw 210, and the lateral arm 1008 of the first linkage portion 1006*a* is received within the groove 1010 defined by the second jaw 212. Receiving the lateral arms 1008 in the grooves 1010 creates a jaw pivot point where the jaws 210, 212 are able to pivot between the open and closed positions. The lateral arms 1008 interact with the corresponding grooves 1010 and help prevent the jaws 210, 212 from separating from each other. In some embodiments, the lateral arms 1008 slidably engage the corresponding grooves 1010 as the jaws 210, 212 open and close about the jaw pivot point, thus the grooves 1010 may operate as corresponding cam surfaces. The jaw pivot points created by interaction between the lateral arms 1008 and the grooves 1010 may be substantially parallel to the pivot axis $P_1$ (FIGS. 6A-6B).

Figure 11:
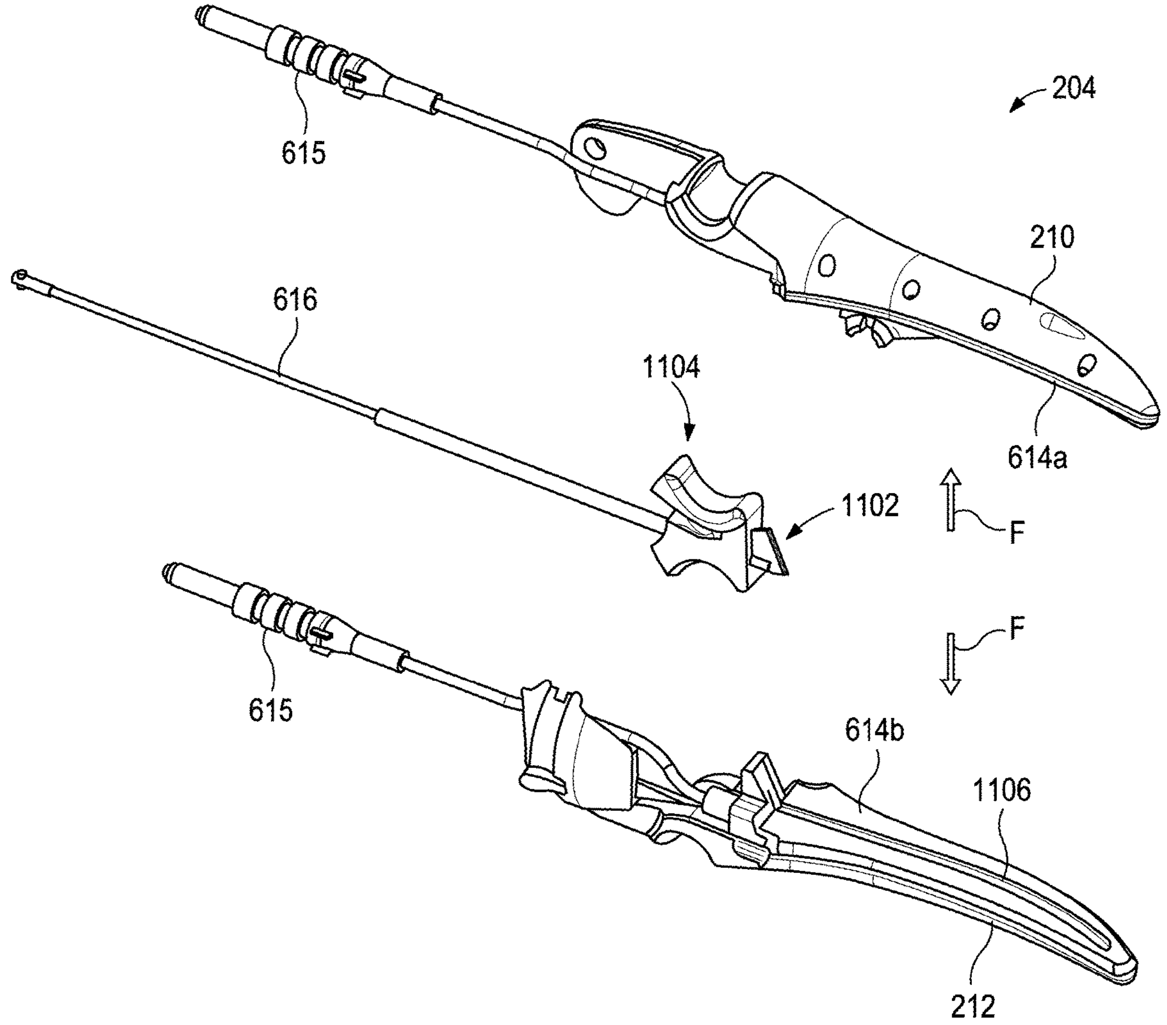
FIG. 11 depicts the end effector in an additional step of disassembly, according to one or more additional embodiments of the present disclosure.

FIG. 11 depicts the end effector 204 in an additional step of disassembly, according to one or more additional embodiments of the present disclosure. More specifically, FIG. 11 shows an exploded view of the end effector 204, where the upper and lower jaws 210, 212 are exploded vertically from each other, as shown by the arrows F, thereby exposing a knife 1102 received within a knife housing 1104. When the end effector 204 is assembled, the knife housing 1104 may be mounted to the end effector 204 between the upper and lower jaws 210, 212. As illustrated, the lower jaw 212 provides or otherwise defines a knife slot 1106 through which the knife 1102 may traverse upon distal actuation of the drive rod 616. While the knife slot 1106 is visible in the lower jaw 212, in some embodiments, the knife slot 1106 may be cooperatively defined by both the upper and lower jaws 210, 212.

The knife 1102 is shown in FIG. 11 in a first or "stowed" position, where the knife 1102 is at least partially received within a cavity defined by the knife housing 1104 and sized to receive and "stow" the knife 1102 when not in use. Upon firing the end effector 204, the drive rod 616 is moved (urged) distally, which correspondingly moves the knife 1102 out of the knife housing 1104 and into the knife slot 1106. After firing is complete, the drive rod 616 is retracted proximally, which pulls the knife 1102 proximally and back into the knife housing 1104 until it is desired to again fire the end effector 204.

At this point, one or more "consumables" of the end effector 204 may be replaced. In some embodiments, for example, one or both of the upper and lower jaws 210, 212 may be replaced, including the corresponding electrodes 614*a,b* and corresponding electrical conductors 612*a,b* and electrical connectors 615. In such embodiments, once the new jaw 210, 212 is provided, the foregoing steps of disassembly and detachment up to this point may be reversed.

In other embodiments, or in addition thereto, the knife 1102 may be replaced. In such embodiments, a new or refurbished knife assembly, including the knife 1102 and the drive rod 616, may be provided together or independently. Once the new knife assembly is provided, the foregoing steps of disassembly and detachment up to this point may be reversed to place the surgical tool 200 (FIG. 2) back into service.

Alternatively, if it is desired to instead replace other or remaining "consumables," such as one or both of the electrodes 614*a,b* or one or both of the jaws 210, 212, the end effector 204 may undergo further disassembly.

Figure 12A:
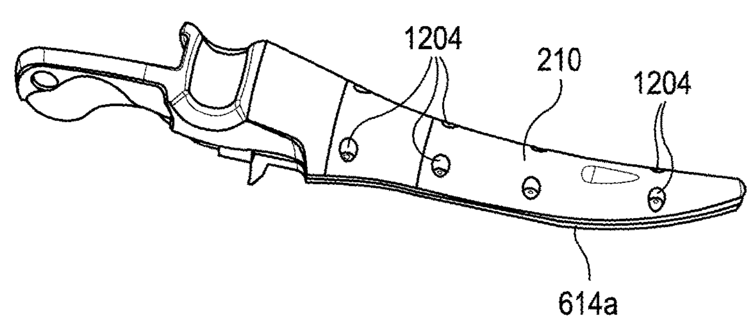
FIGS. 12A-12C are views of further disassembly and subsequent assembly of the upper jaw, according to one or more embodiments.
Figure 12B:
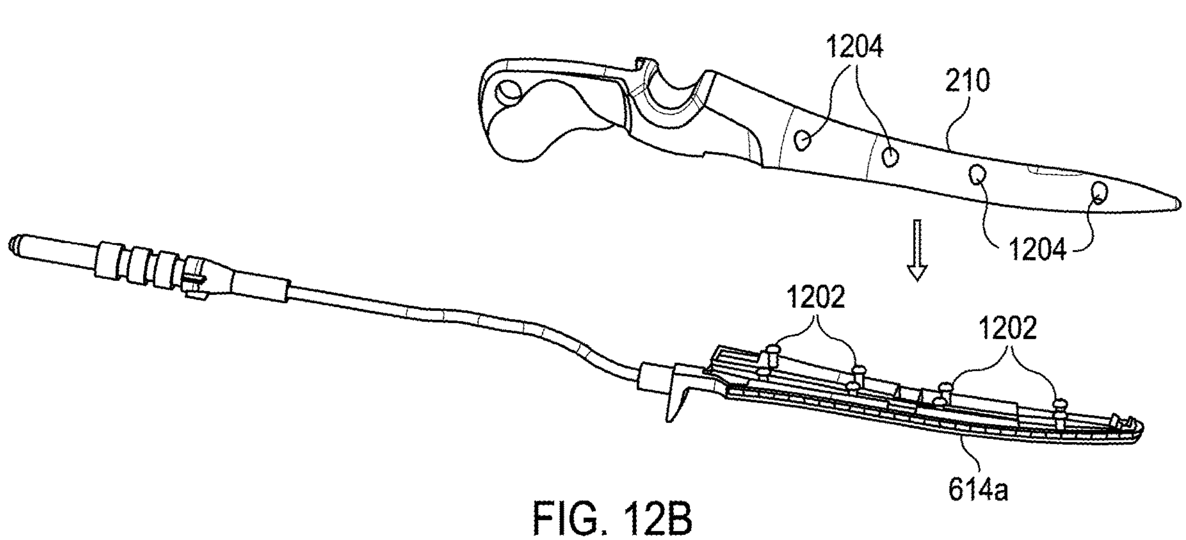
Figure 12C:
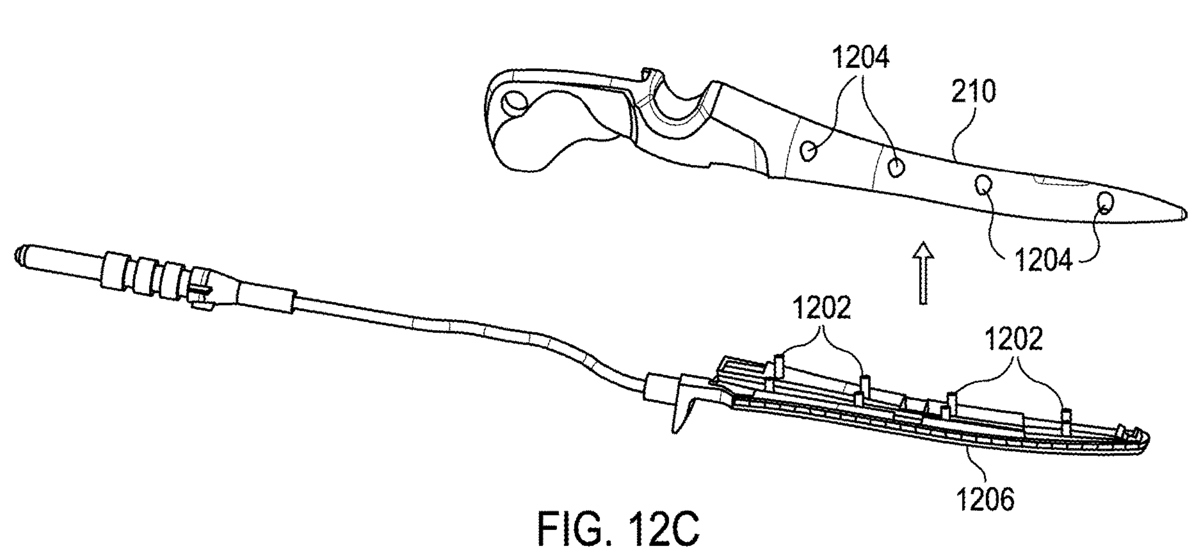

FIGS. 12A-12C are progressive views of further disassembly and subsequent assembly of the upper jaw 210, according to one or more embodiments. It should be noted that while the upper jaw 210 is shown in FIGS. 12A-12C, the following discussion is equally applicable to the lower jaw 212.

In some embodiments, it may be desired to replace the upper electrode 614*a* coupled to and forming part of the upper jaw 210. The upper electrode 614*a* may be manufactured via an injection molding process that results in the creation of a plurality of vertical posts 1202 (see FIG. 12B). The posts 1202 may be alignable with a corresponding plurality of orifices 1204 defined in the body of the upper jaw 210, and the upper electrode 614*a* may be secured to the body of the upper jaw 210 by heat staking the posts 1202 within the orifices 1204. Heat staking the posts 1202 applies heat to the posts 1202 while simultaneously applying force to deform the posts 1202 and thereby form heads that secure the posts 1202 within the orifices 1204. As will be appreciated, however, the upper electrode 614*a* may be manufactured from or secured to the body of the upper jaw 210 by other manufacturing methods and means, without departing from the scope of the disclosure.

To remove the upper electrode 614*a* from the body the upper jaw 210, as shown in FIG. 12B, the posts 1202 may be drilled, milled, or punched out. This may be accomplished by accessing the heads or upper ends of the posts 1202 via the corresponding orifices 1204, and then drilling, milling, or punching out the heads of the posts 1202. This process disengages the posts 1202 from the orifices 1204 and thereby allows the upper electrode 614*a* to separate from the body of the upper jaw 210.

Once the old upper electrode 614*a* is removed, a new upper electrode 1206 may be attached to the body of the upper jaw 210, as shown in FIG. 12C. In some embodiments, the new upper electrode 1206 may be attached to the body of the upper jaw 210 via heat staking. More specifically, as illustrated, the new upper electrode 1206 may include a plurality of posts 1202 configured to align with the orifices 1204 defined in the body of the upper jaw 210. Once properly received within the orifices 1204, the posts 1202 may be secured to the body of the upper jaw 210 by heat staking the posts 1202, as generally described above. The straightness of the new electrode 1206 relative to the upper jaw 210 can be maintained while heat staking the individual posts. In other embodiments, however, the new upper electrode 1206 may be bonded to the body of the upper jaw 210 with an epoxy. In some embodiments, the new upper electrode 1206 may have a new anti-stick coating on it.

The foregoing steps of disassembly and detachment of the end effector 204 up to this point may then be reversed to place the surgical tool 200 (FIG. 2) back into service. In particular, in a process that reverses the process outlined in FIG. 11 above, the upper and lower jaws 210, 212 may be brought into vertical contact with each other and thereby capturing the knife 1102 and the knife housing 1104 therebetween.

Moreover, in a process that reverses the process outlined in FIGS. 10A-10B above, the linkage portions 1006*a,b* of the distal linkage 604 may be assembled to the jaws 210, 212, and the securing band 1002 may be re-attached or re-secured. In some embodiments, the securing band 1002 may be re-attached to the distal linkage 604 via spot welding, but could alternatively be attached by other means, such as brazing, mechanical fasteners, a mechanical engagement, or any combination of the foregoing.

In a process that reverses the process outlined in FIG. 7A above, the pulleys 606*a,b* may then be re-mounted to the first and second jaw extensions 702*a,b*.

In a process that reverses the process outlined in FIGS. 7B and 8 above, the drive rod 616 may then be re-attached and re-coupled to the push rod 708.

Figures 13A, 13B:
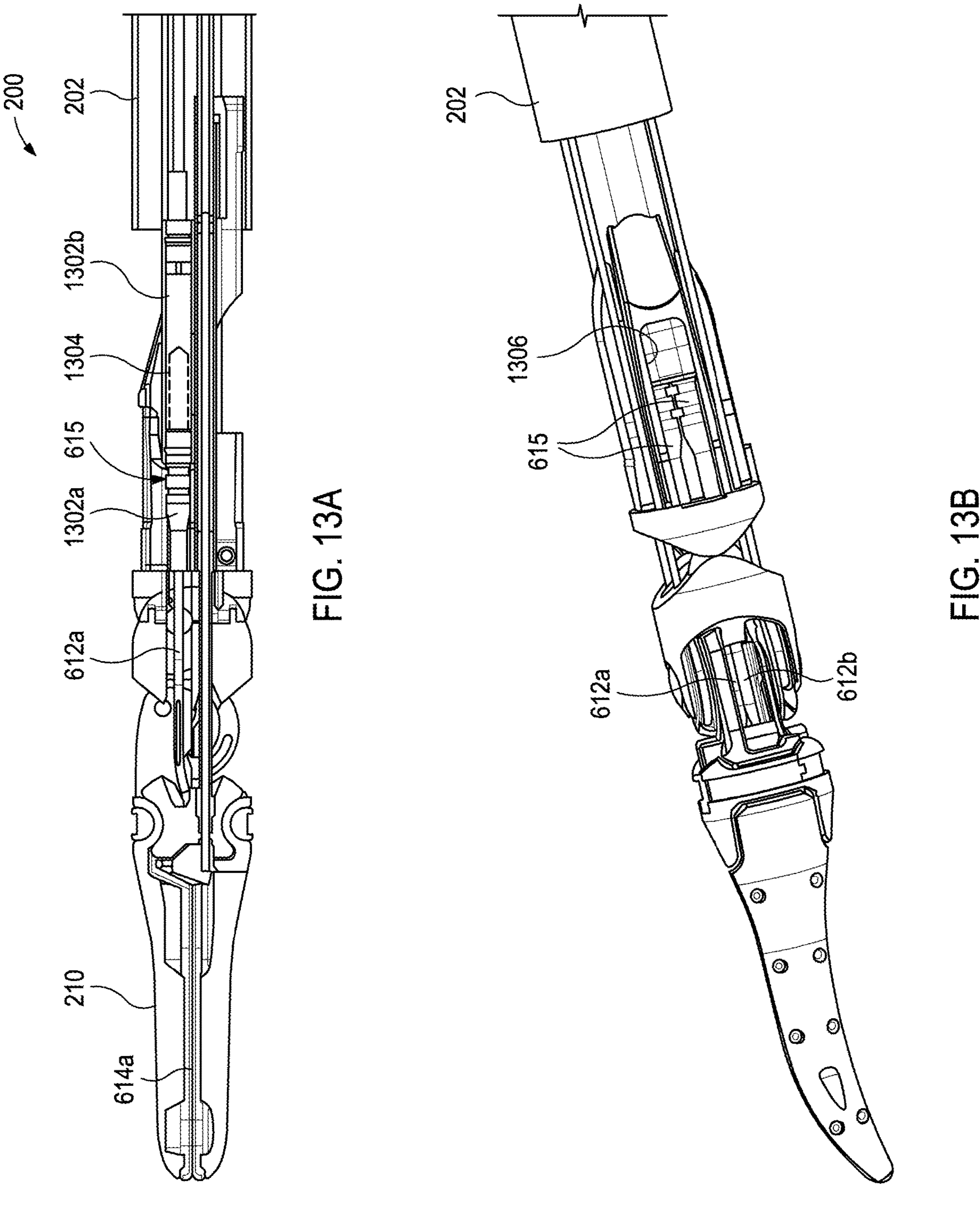
FIGS. 13A and 13B are cross-sectional side and isometric views, respectively, of the distal end of the surgical tool depicting interconnection of the electrical conductors, according to one or more embodiments.

In a process that reverses the process outlined in FIG. 9 above, distal lengths of the electrical conductors 612*a,b* may then be re-connected to proximal lengths of the electrical conductors 612*a,b* by re-attaching the electrical connectors 615. FIGS. 13A and 13B are cross-sectional side and isometric views, respectively, of the distal end of the surgical tool 200 depicting interconnection of the electrical conductors 612*a,b*, according to one or more embodiments. More particularly, FIGS. 13A-13B depict the shaft 202 retracted proximally to enable the reassembly technician to access the electrical connectors 615.

FIG. 13A depicts the electrical connector 615 for the first electrical conductor 612*a* and includes a first or "distal" connector 1302*a* and a second or "proximal" connector 1302*b*. While the electrical connector 615 for the first electrical conductor 612*a* is shown in FIG. 13A, the following discussion is equally applicable to the electrical connector 615 for the second electrical conductor 612*b*. As illustrated, the distal connector 1302*a* is attached to a distal length (portion) of the first electrical conductor 612*a*, which extends to the upper electrode 614*a* and is attached to the upper jaw 210. The proximal connector 1302*b* is attached to a proximal length (portion) of the first electrical conductor 612*b*, which extends to the drive housing 208 (FIGS. 2 and 4). As mentioned above, the electrical connector 615 may comprise an interference fit plug, such as a banana style clip. Accordingly, the distal and proximal connectors 1302*a,b* may be detached (disconnected) by merely pulling in opposite directions, as generally described above.

Reattaching the distal and proximal connectors 1302*a,b* may be accomplished by reversing the detachment process. In particular, the distal connector 1302*a* may include a male end 1304 (shown in dashed lines) receivable within a corresponding female receptacle provided and otherwise defined by the proximal connector 1302*b*. Receiving the male end 1304 within the female receptacle will properly connect the distal and proximal connectors 1302*a,b*. In some embodiments, however, the male end 1304 may alternatively be provided on the proximal connector 1302*b*, and the female receptacle may instead be provided on the distal connector 1302*a*, without departing from the scope of the disclosure.

Referring to FIG. 13B, a window 1306 may be defined and otherwise provided in the subassembly within the shaft 202. The window 1306 may provide physical access to the electrical connectors 615, thereby allowing a technician to not only disconnect the distal and proximal connectors 1302*a,b* (FIG. 13A), but to also visually ensure that the distal and proximal connectors 1302*a,b* successfully mate. In at least one embodiment, the window 1306 may also allow the technician to use a tool (not shown) to properly mate the distal and proximal connectors 1302*a,b*.

Figure 14:
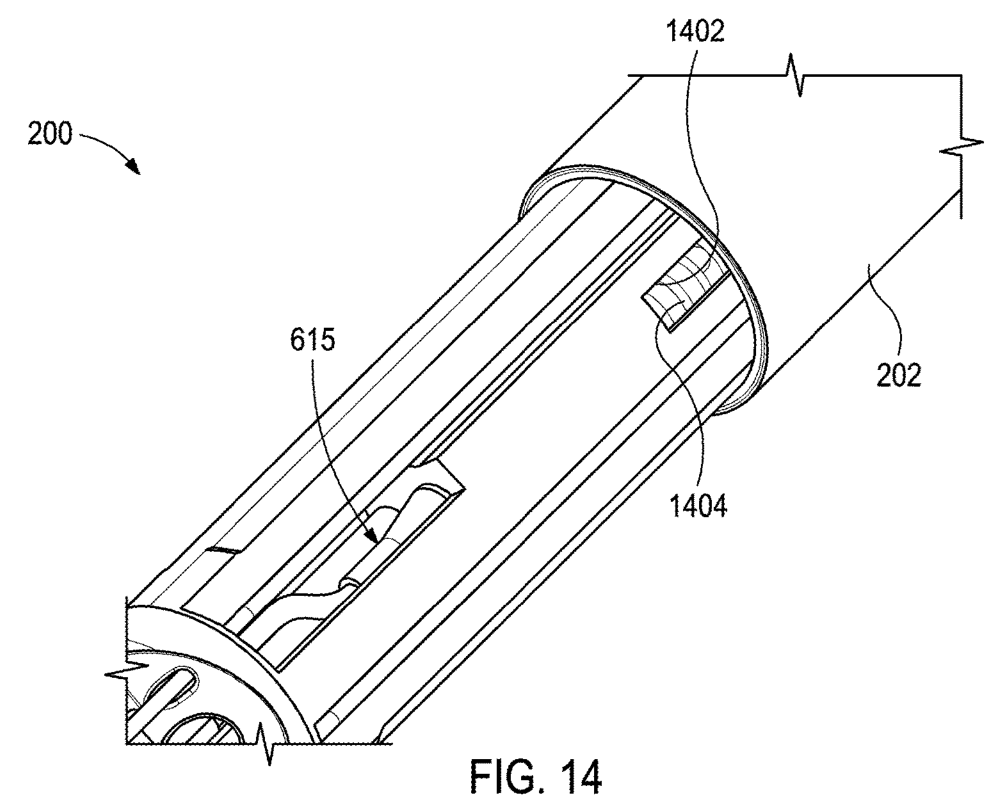
FIG. 14 is another isometric view of the distal end of the surgical tool, according to one or more additional embodiments.

FIG. 14 is another isometric view of the distal end of the surgical tool 200, according to one or more additional embodiments. In particular, FIG. 14 depicts an alternative embodiment for the electrical connectors 615 (one partially shown) and an example reattachment process. As illustrated, a window 1402 may be defined and otherwise provided in the subassembly within the shaft 202. The window 1402 may provide physical access to the electrical connectors 615, which allows a technician to visually ensure proper reattachment and connection of the electrical connectors 615. In the illustrated embodiment, the electrical connector 615 may include a biasing device or spring 1404. In such embodiments, the electrical connector 615 may be spring-tensioned, and reattaching the electrical connector 615 may require overcoming the spring force of the spring 1404. Accordingly, in at least one embodiment, the window 1402 may further be used to insert a tool configured to help disconnect the electrical connector 615 during disassembly and to secure the connection of the electrical connector 615 during assembly. The springs 1404 may prove advantageous in helping to maintain tension on the electrical conductors as they pass through the wrist while the wrist is in various angular positions or poses. These spring-loaded electrical connectors 615 have a cylindrical connection means to ensure they do not come apart due to the spring force, and may further include seals (e.g., O-rings) that help prohibit fluid ingress into the electrical connector 615.

Once the electrical connectors 615 are properly reattached, the end effector 204 may be advanced proximally to be remounted to the distal clevis 602, in a process that reverses the process outlined in FIGS. 6A-6B above. During this process, the pulleys 606*a,b* may then be re-mounted and otherwise received by open-ended slots 620 of the distal clevis 602, and thereby returning the end effector 204 to the assembled state.

In a process that reverses the process outlined in FIGS. 5A-5B above, the shaft 202 may then be manually moved distally and otherwise back toward the end effector 204.

Finally, in a process that reverses the process outlined in FIG. 4 above, the surgical tool 200 may be detached and removed from the disassembly fixture 402.

Figure 15:
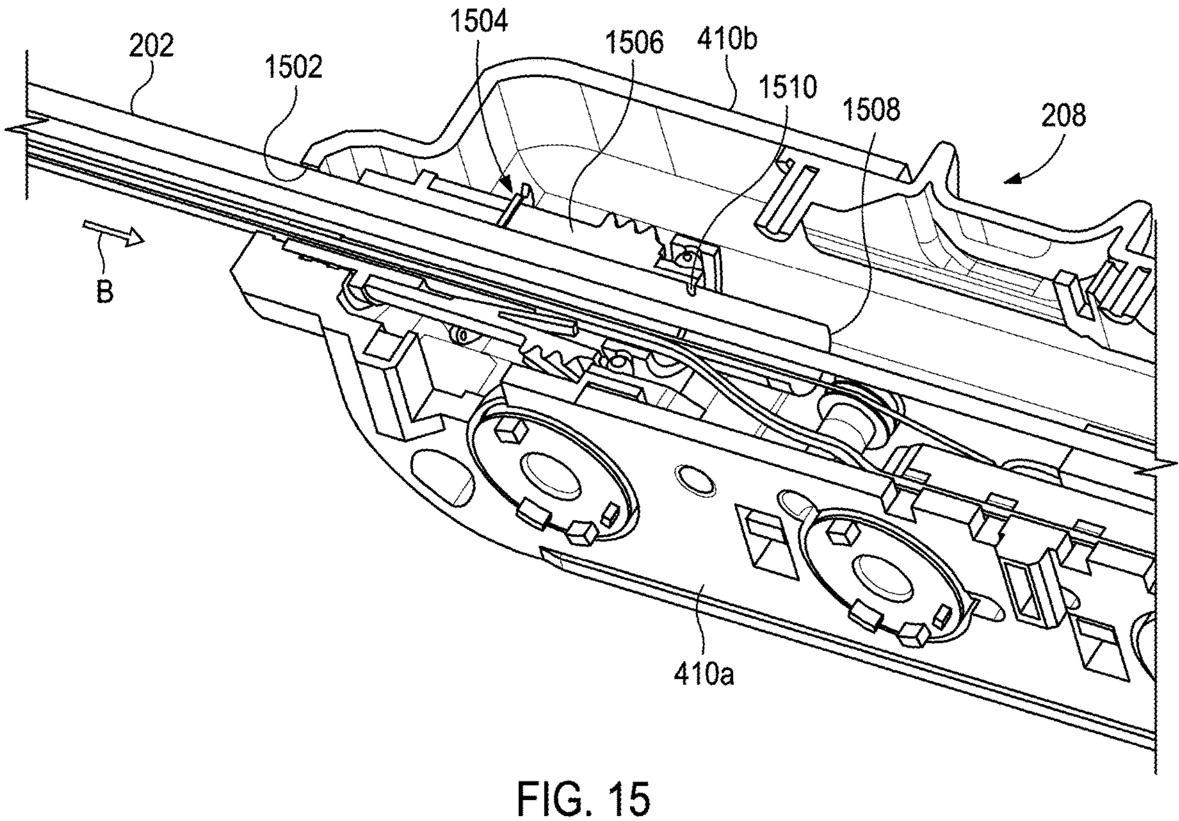
FIG. 15 is a cross-sectional side view of the drive housing, according to one or more embodiments.

FIG. 15 is a cross-sectional side view of the drive housing 208, according to one or more embodiments. More specifically, FIG. 15 depicts the interior of the drive housing 208. As illustrated, the shaft 202 extends through an aperture 1502 defined in the drive housing 208 and extends distally therefrom. One or more retention clips 1504 (one shown) may be mounted within the interior of the drive housing 208 and configured to secure the shaft 202 at a distal position. In the illustrated embodiment, the retention clip 1504 may be secured to a shaft collar 1506 arranged within the interior the drive housing 208, but could alternatively be secured to other features or structures within the drive housing 208.

When the shaft 202 is in its distal-most position, as shown in FIGS. 2, 4, and 5A, the retention clip 1504 may be arranged to abut or engage a proximal end 1508 of the shaft 202, thereby preventing the shaft 202 from moving in the proximal direction B. In other embodiments, however, the retention clip 1504 may be configured to engage another portion of the shaft 202 and equally prevent its proximal movement, such as being received within a groove 1510 defined on the body of the shaft 202.

To be able to move the shaft 202 proximally B, as described in the process outlined in FIGS. 5A and 5B above, the retention clip 1504 must either be removed or flexed out of engagement with the proximal end 1508 (or the groove 1510). In some embodiments, the retention clip 1504 may comprise a C-clip or the like. In such embodiments, the retention clip 1504 may be manually removed by a technician and otherwise flexed out of engagement with the proximal end 1508 (or the groove 1510). Those skilled in the art, however, will readily recognize that the retention clip 1504 may comprise other types of mechanical components or devices capable of securing the shaft 202 in its distal-most position, without departing from the scope of the disclosure.

In FIG. 15, the shaft 202 has been moved in the proximal direction B after successfully disengaging the retention clip 1504 from the proximal and 1508 (or the groove 1510). Once the retention clip 1504 is removed, the shaft 202 may be free to move in the proximal direction B. A technician may be able to access the retention clip 1504 by removing one or both of the bottom and upper surfaces 410*a*, 410*b* of the drive housing 208. Once the bottom or upper surfaces 410*a,b* is/are removed, a technician may easily access and manually manipulate the retention clip 1504.

Figure 16:
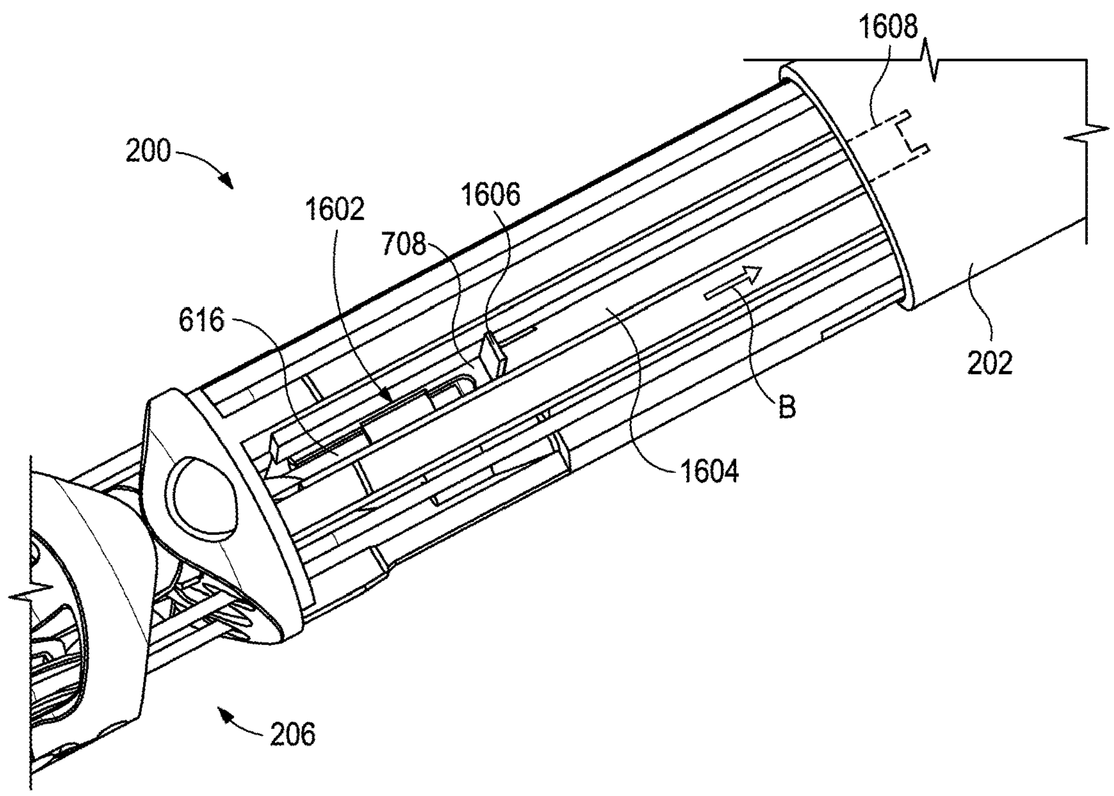
FIG. 16 is an isometric view of the distal end of the surgical tool, according to one or more additional embodiments.

FIG. 16 is an isometric view of the distal end of the surgical tool 200, according to one or more additional embodiments. In the illustrated embodiment, the shaft 202 is retracted proximally, thereby exposing various subcomponents of the surgical tool 200 at or near the wrist 206, including a releasable interconnection 1602 between the drive rod 616 and the push rod 708. The releasable interconnection 1602 may be the same as or different from the bayonet-style connection described above with reference to FIG. 8. In at least one embodiment, the releasable interconnection 1602 may comprise a spring-loaded interconnection capable of being released by manually releasing the spring tension, for example.

In some embodiments, as illustrated, the surgical tool 200 may further include a shaft sleeve 1604 that is translatable longitudinally along at least a portion of the shaft 202 and otherwise retractable to expose the releasable interconnection 1602. As illustrated, the shaft sleeve 1604 includes a vertical tab 1606, which can be moved proximally to expose the releasable interconnection 1602. In some embodiments, a technician may be able to manually engage the vertical tab 1606 to force (slide, shift, etc.) the shaft sleeve 1604 in the proximal direction B. In other embodiments, however, the vertical tab 1606 may be interlocked with a sleeve connector 1608 (shown in dashed lines) provided on the shaft 202. In such embodiments, moving the shaft 202 in either direction (distal or proximal) correspondingly acts on the vertical tab 1606 and causes the shaft sleeve 1604 to move in the same direction. In yet other embodiments, the vertical tab 1606 may not be interlocked with the sleeve connector 1608, but instead merely engageable therewith. In such embodiments, a technician may need to manually engage the vertical tab 1606 to move the shaft sleeve 1604 proximally B, but moving the shaft 202 distally engages the sleeve connector 1608 on the vertical tab 1606 and correspondingly acts on the vertical tab 1606 and causes the shaft sleeve 1604 to move in the same distal direction.

Once the shaft sleeve 1604 is moved proximally to expose the releasable interconnection 1602, the technician may then manually disengage the drive rod 616 from the push rod 708 by releasing the releasable interconnection 1602, or otherwise verify that the drive rod 616 is successfully disengaged from the push rod 708. Moreover, once the drive rod 616 is released from the push rod 708, the drive rod 616 and the interconnected knife 1102 (FIG. 11) may be removed distally while the wrist 206 (articulation joint assembly) remains intact. In embodiments that include the sleeve connector 1608, the vertical tab 1606 may be held distally when the shaft 202 is in its distal-most position. In such embodiments, the shaft 202 operates as an outer insulative sleeve and a metallic shaft may be arranged within the shaft 202 and may provide an opposing tab that contacts the vertical tab 1606 when the shaft 202 is in its distal-most position. This may prove advantageous in helping to ensure that the releasable interconnection 1602 is connected whenever the shaft 202 is fully distal (i.e., during operation of the device).

Figure 17:
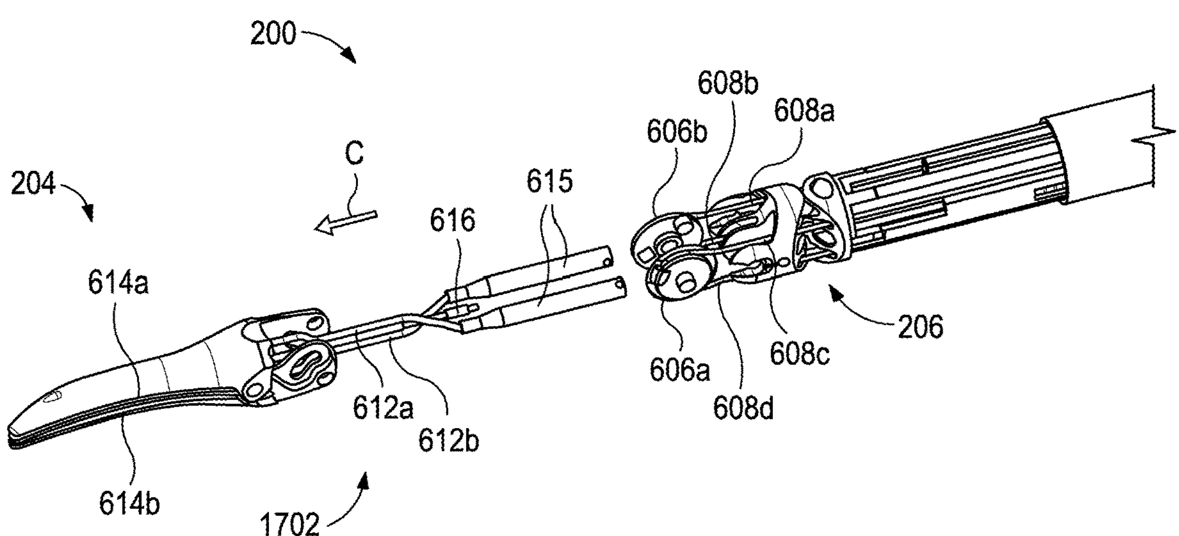
FIG. 17 is an isometric view of the distal end of the surgical tool, according to one or more additional embodiments.

FIG. 17 is an isometric view of the distal end of the surgical tool 200, according to one or more additional embodiments. The surgical tool 200 includes a jaw assembly 1702, which includes the end effector 204, the drive rod 616 (and interconnected knife), the electrical conductors 612*a,b* and associated electrodes 614*a,b*, and the electrical connectors 615. FIG. 17 depicts the jaw assembly 1702 separated from the wrist 206 (articulation joint assembly). According to embodiments of the present disclosure, this can be accomplished while the wrist 206 remains intact.

In a first step, for example, the jaw assembly 1702 may be advanced in the distal direction C along with the pulleys 606*a,b* and corresponding drive cables 608*a-d*. As described above with reference to FIGS. 6A-6B, the pulleys 606*a,b* may be detached from the distal clevis 602 by pulling distally, thereby removing the end caps 622 from the open-ended slots 620 of the distal clevis 602. In a second step, the jaw assembly 1702 may be further advanced in the distal direction C, thereby separating the jaw assembly 1702 from the pulleys 606*a,b* as generally described above with reference to FIG. 7A. In this (preferred) embodiment, the disassembly steps would be to first retract the shaft 202, disconnect the electrical connections and knife interconnection and then advance the wrist assembly 206 and pulleys 606*a,b* followed by separating the pulleys 606*a,b* to fully remove the end effector 204.

Threaded Knife Member Attachment

One area that causes issues for vessel sealers, such as the end effector 204 described herein, is the dulling of the knife 1102 (FIG. 11) during procedural use. As described herein, the knife assembly, including the knife 1102 and the interconnected drive rod 616 (FIGS. 6A-6B), may be characterized either jointly or individually as a "consumable," which may have a limited or predetermined lifespan. What is needed is a method of replacing the knife 1102 in order to maximize reuse of components for circularity, while maintaining consistent cutting performance.

Figure 18:
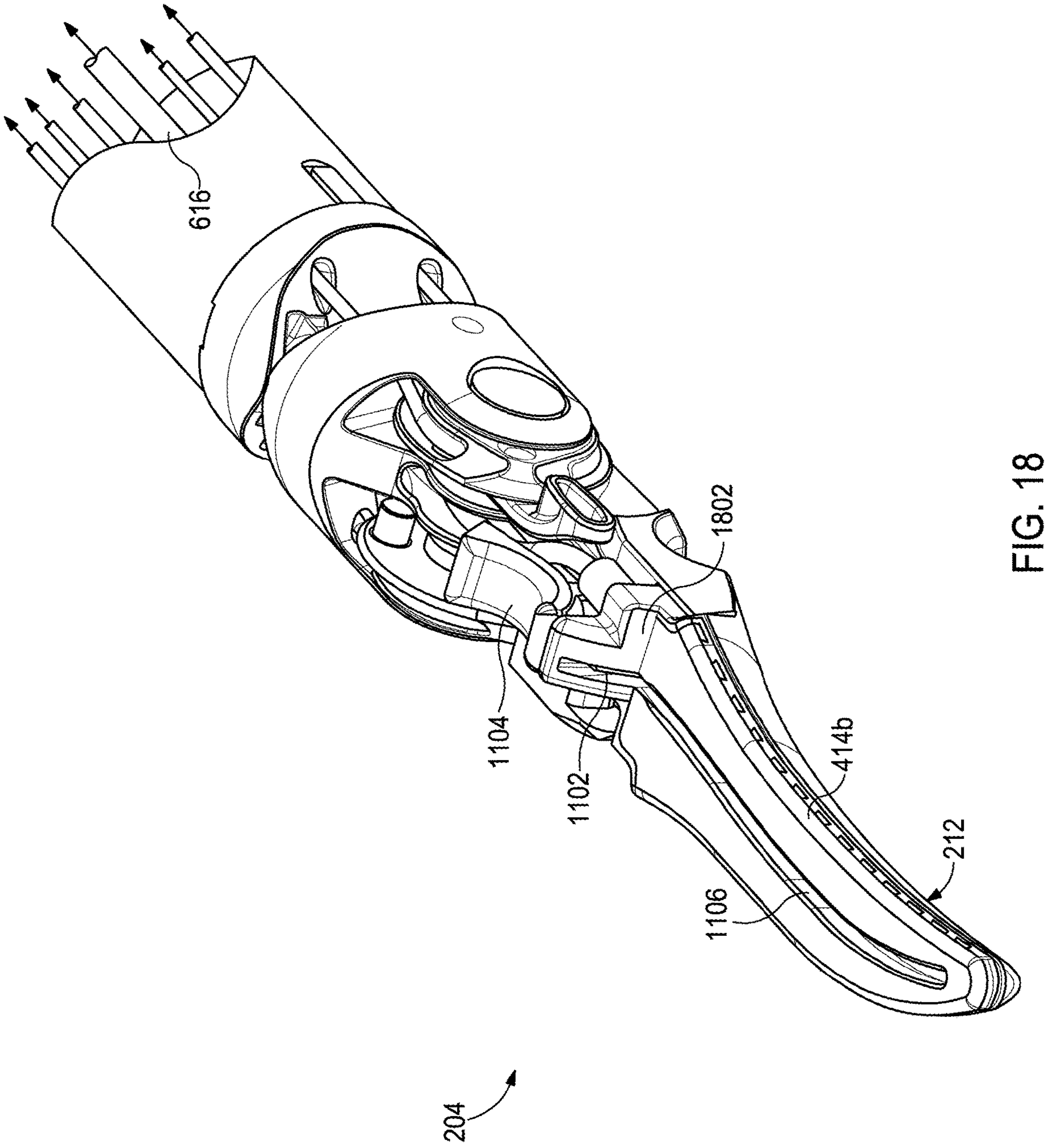
FIG. 18 is another enlarged isometric view of the end effector, according to one or more embodiments of the present disclosure.

FIG. 18 is another enlarged isometric view of the end effector 204, according to one or more embodiments of the present disclosure. The upper jaw 210 (FIGS. 2 and 6A-6B) is omitted from FIG. 18 to enable viewing of various internal features of the end effector 204.

In the illustrated embodiment, the knife 1102 (mostly occluded) is shown received within a portion of the lower electrode 414*b* of the lower jaw 212 and, more particularly, within a portion of an insulator 1802 coupled to the lower electrode 414*b*. In its retracted position, as shown in FIG. 18, the knife 1102 may also be partially received within the knife housing 1104 mounted to the end effector 204 between the upper and lower jaws 210, 212. The lower jaw 212 provides or otherwise defines at least a portion of the knife slot 1106 through which the knife 1102 may traverse upon distal actuation of the drive rod 616. As mentioned above, however, in some embodiments, the knife slot 1106 may be cooperatively defined by both the upper and lower jaws 210, 212.

As described in more detail below, the knife housing 1104 defines a central passageway through which the drive rod 616 is able to extend to move the knife 1102 along the knife slot 1106. Upon firing the end effector 204, the drive rod 616 is moved (urged) distally, which correspondingly moves the knife 1102 out of the knife housing 1104 and into the knife slot 1106. After firing is complete, the drive rod 616 is retracted proximally, which pulls the knife 1102 proximally and back into the knife housing 1104 until it is desired to again fire the end effector 204.

Figure 19A:
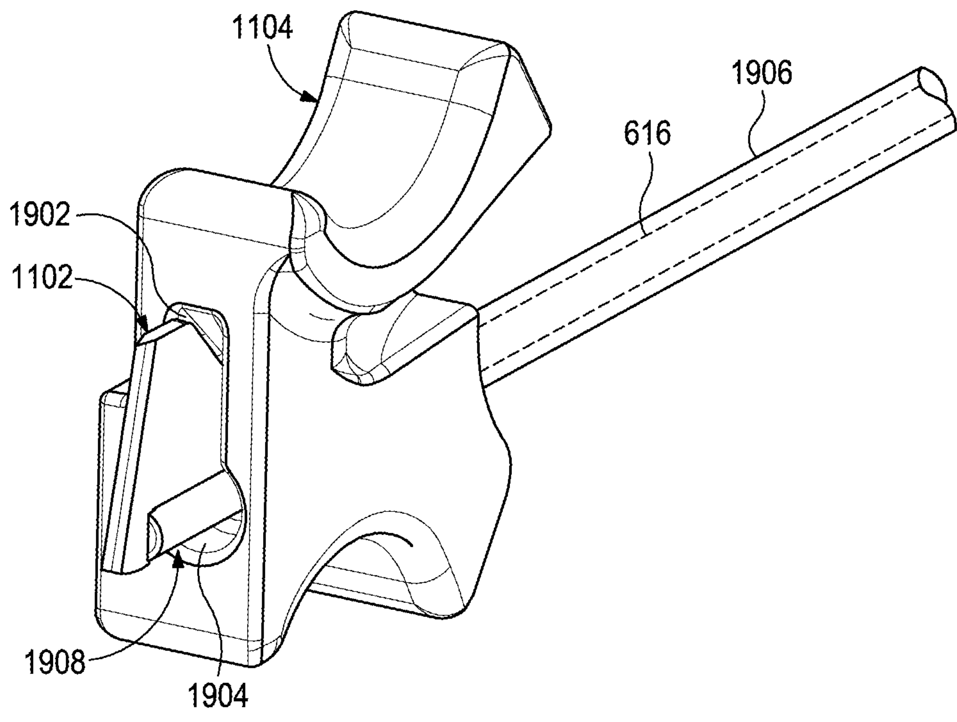
FIGS. 19A and 19B are enlarged isometric views of the knife and the knife housing of FIG. 18, according to one or more embodiments.
Figure 19B:
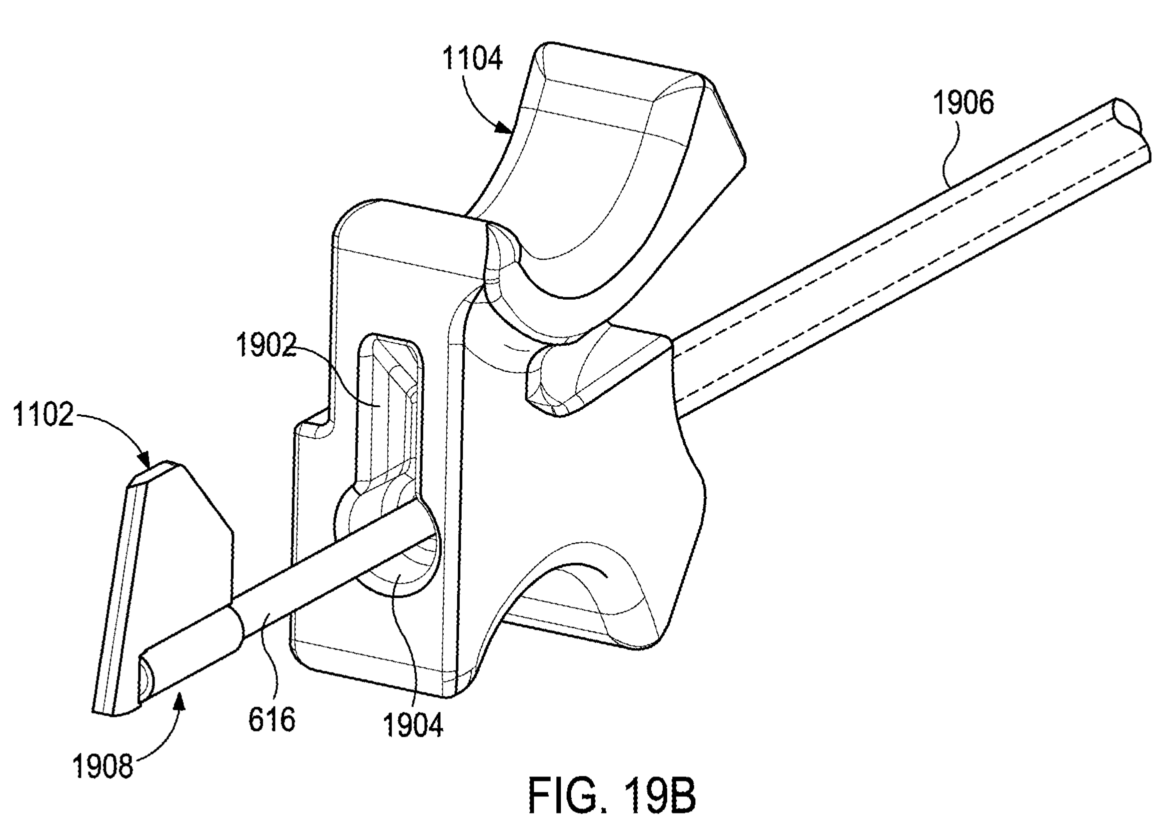

FIGS. 19A and 19B are enlarged isometric views of the knife 1102 and the knife housing 1104, according to one or more embodiments. In FIG. 19A, the knife 1102 is shown in a first or "stowed" position, where the knife 1102 is at least partially received within a cavity 1902 defined by the knife housing 1104 and sized to receive and "stow" the knife 1102 when not in use. In FIG. 19B, the knife 1102 is shown in a second or "extended" position, where the knife 1102 is extended distally out of the cavity 1902.

As mentioned above, the knife 1102 may be operatively coupled to the distal end of the drive rod 616 (shown in dashed lines in FIG. 19A). A central passageway 1904 is defined through the knife housing 1104 and provides a conduit through which the drive rod 616 is able to extend to move the knife 1102 into and along the knife slot 1106 (FIG. 18). In at least one embodiment, the cavity 1902 may form part of or communicate with the central passageway 1904. In some embodiments, the drive rod 616 may comprise a solid shaft, but may alternatively comprise a tube or tubular structure. Moreover, the drive rod 616 may be made of a variety of flexible materials including, but not limited to, a metal or metal alloy (e.g., a nickel-titanium alloy or "nitinol"), a plastic or thermoplastic material, a composite material, or any combination thereof. The drive rod 616 may also comprise a braided cable construction of a metal (e.g., stainless steel, tungsten, etc.), or any of the aforementioned materials, and such braided cable may be radially constrained to support axial loads.

In some embodiments, as illustrated, a flexible sheath 1906 (e.g., a hypotube or the like) may cover at least a portion of the drive rod 616. The sheath 1906 may support and help prevent buckling of the drive rod 616 when assuming compressive loads during articulation of the wrist 206 (FIGS. 2 and 6A-6B) and opening and closure of the jaws 210, 212 (FIGS. 2 and 6A-6B). Similar to the drive rod 616, the flexible sheath 1906 may be made of a variety of flexible materials including, but not limited to, a metal or metal alloy (e.g., a nickel-titanium alloy or "nitinol"), a metallic coil, a plastic or thermoplastic material, a composite material, a braided tubular, or any combination thereof.

Upon firing the end effector 204 (FIGS. 2 and 6A-6B), the drive rod 616 is moved (urged) distally through the central passageway 1904, which correspondingly moves the knife 1102 to the extended position and otherwise out of the cavity 1902 and into the knife slot 1106 (FIG. 18). As the drive rod 616 translates distally, the sheath 1906 supports the drive rod 616 against axial buckling resulting from compressive loading on the drive rod 616. After firing is complete, the drive rod 616 is retracted proximally, which correspondingly pulls the knife 1102 proximally and back to the stowed position and otherwise into the cavity 1902 until it is desired to again fire the end effector 204.

The knife 1102 may be attached to the distal end of the drive rod 616 at a connecting or "retention" feature 1908. As described herein, the retention feature 1908 may be configured to removably couple the knife 1102 to the drive rod 616. For example, the retention feature 1908 may be secured to the knife 1102, but may be threadably engaged to the distal end of the drive rod 616 and, therefore, capable of being unthreaded from the drive rod 616.

Figure 20A:
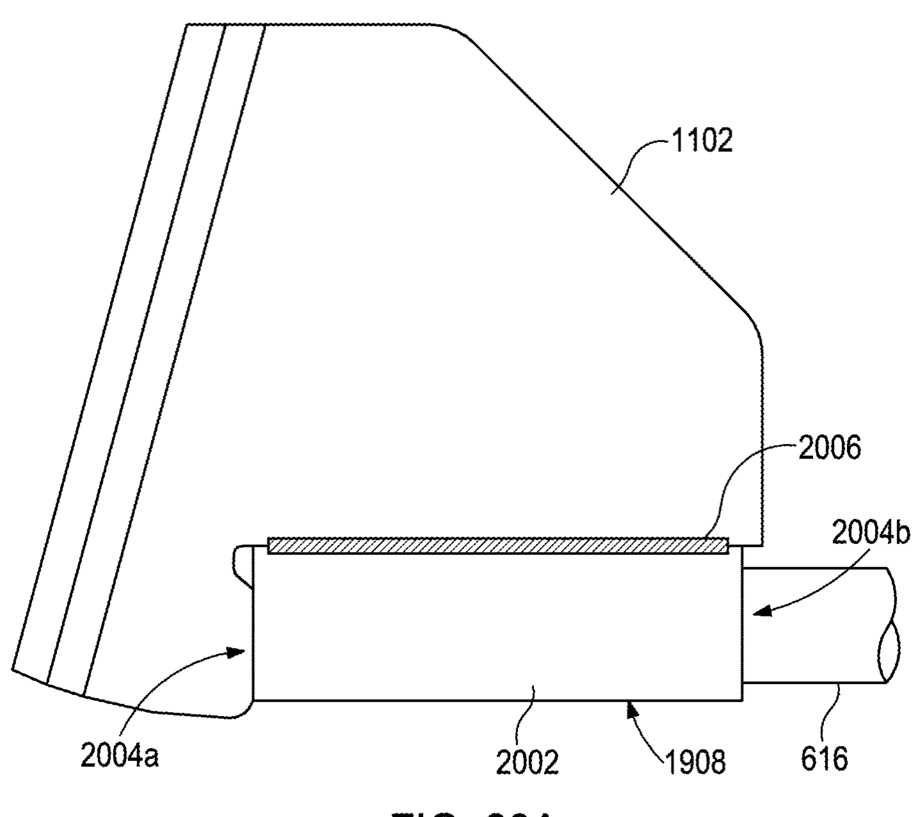
FIGS. 20A and 20B are side views of the knife coupled to the distal end of the drive rod, according to one or more embodiments.
Figure 20B:
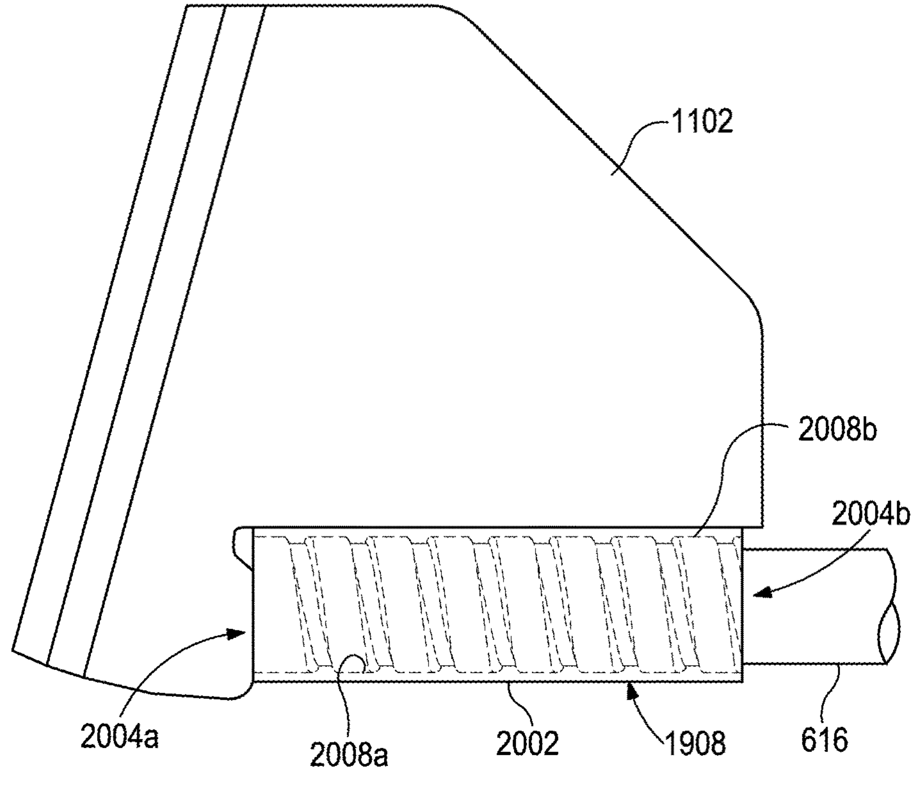

FIGS. 20A and 20B are side views of the knife 1102 as coupled to the distal end of the drive rod 616, according to one or more embodiments. The retention feature 1908 may comprise a short tubular length or tube. More specifically, the retention feature 1908 may comprise a tubular body 2002 having a first or "distal" end 2004*a* and a second or "proximal" end 2004*b* opposite the distal end 2004*a*.

As best seen in FIG. 20A, the knife 1102 may be welded to the retention feature 1908 at a weld 2006 placed at the interface between the knife 1102 and the retention feature 1908. The retention feature 1908 may be made of a material capable of allowing the knife 1102 to be welded thereto. In at least one embodiment, for example, the retention feature 1908 may be made of a metal, such as stainless steel. In embodiments where the knife 1102 is made of Nitinol, the retention feature 1908 may also be made of Nitinol.

Referring to FIG. 20B, the tubular body 2002 may provide an inner conduit or passageway extending at least partially between the distal and proximal ends 2004*a,b*. The inner passageway defines internal threading 2008*a* (shown in dashed lines) configured to threadably mate with external threading 2008*b* (shown in dashed lines) defined on the distal end of the drive rod 616. The internal and external threading 2008*a,b* may comprise any type of threading suitable to threadably attach the tubular body 2002 to the distal end of the drive rod 616, and may include, but is not limited to, roll-formed thread, unified miniature thread (UNM), standard thread, ACME thread, custom threading, or any combination of the foregoing.

Accordingly, the knife 1102 may be threadably attached to the distal end of the drive rod 616 at the threaded engagement between the internal and external threading 2008*a,b*. The threaded connection between the tubular body 2002 and the drive rod 616 constrains the positioning of the knife 1102 and transfers cutting loads along the axis of the drive rod 616. In embodiments where it is desired to replace the knife 1102, the knife 1102 may merely be unthreaded from the distal end of the drive rod 616 and a new knife may be threaded back onto the distal end.

Figure 21A:
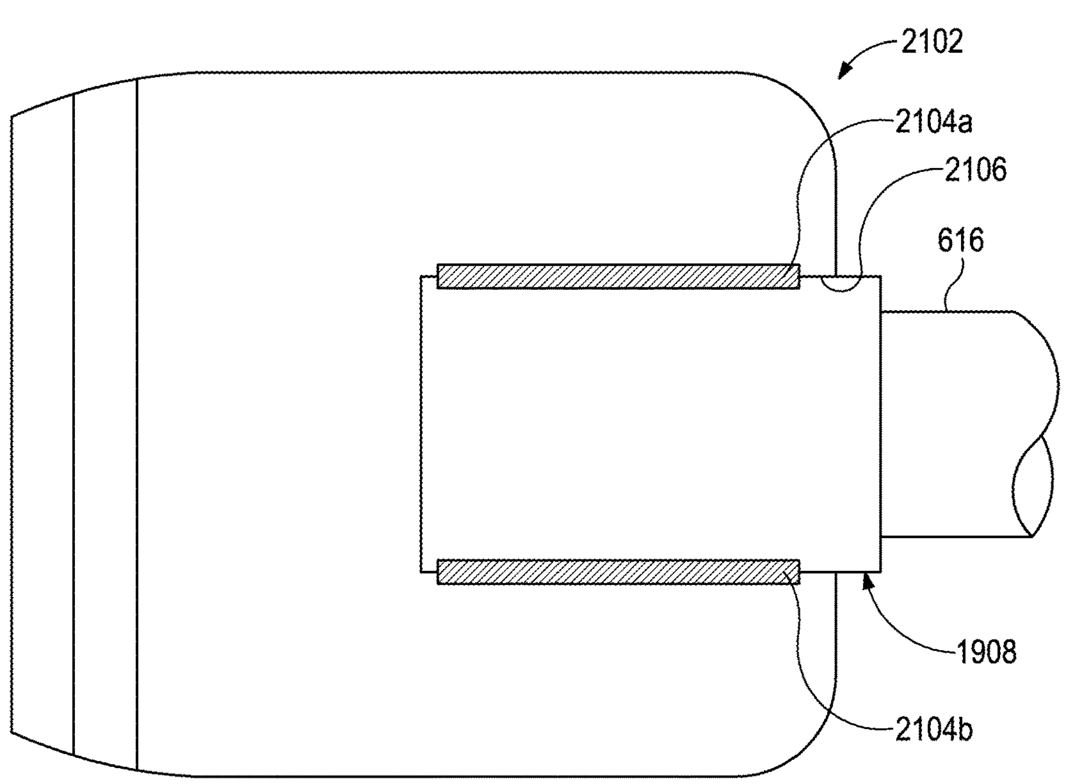
FIGS. 21A and 21B are side views of another example knife, as coupled to the distal end of the drive rod, according to one or more additional embodiments.
Figure 21B:
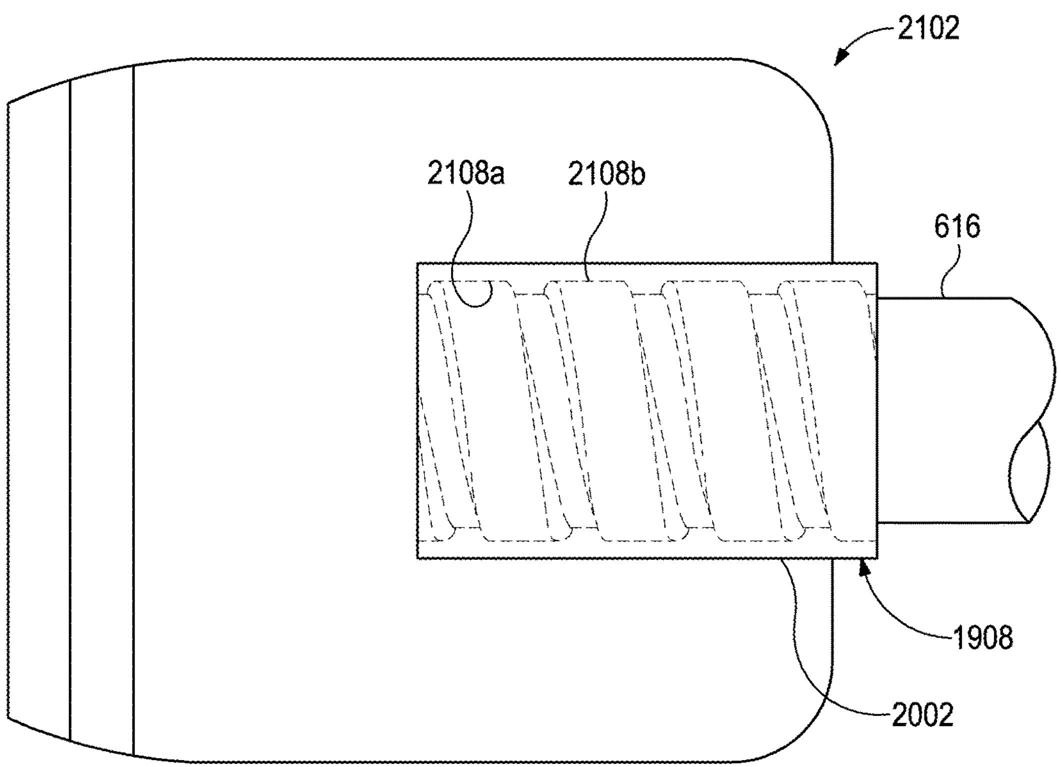

FIGS. 21A and 21B are side views of another example knife 2102, as coupled to the distal end of the drive rod 616, according to one or more additional embodiments. The knife 2102 may be similar in some respects to the knife 1102 of FIGS. 20A-20B, and therefore may be best understood with reference thereto, where like numerals will represent like components not described again in detail.

The knife 2102 includes the retention feature 1908, and as best seen in FIG. 21A, the knife 2102 may be welded to the retention feature 1908 at one or more welds, shown as a first weld 2104*a* and a second weld 2104*b*. More specifically, the knife 2102 may define a notch or cutout 2106 that extends into a central portion of the body of the knife 2102 from its proximal end, and the retention feature 1908 may be sized to be received within the cutout 2106. Once received within the cutout 2106, one or both of the welds 2104*a,b* may be applied at corresponding interfaces between the knife 2102 and the retention feature 1908. In at least one embodiment, only one of the welds 2104*a,b* may be needed or included.

Referring to FIG. 21B, the tubular body 2002 of the retention feature 1908 may provide an inner conduit or passageway that defines internal threading 2108*a* (shown in dashed lines) configured to threadably mate with external threading 2108*b* (shown in dashed lines) defined on the distal end of the drive rod 616. The internal and external threading 2108*a,b* may be similar to the threading 2008*a,b* of FIG. 20B and, therefore, may comprise any type of threading suitable to threadably attach the tubular body 2002 to the distal end of the drive rod 616.

Figures 22A, 22B:
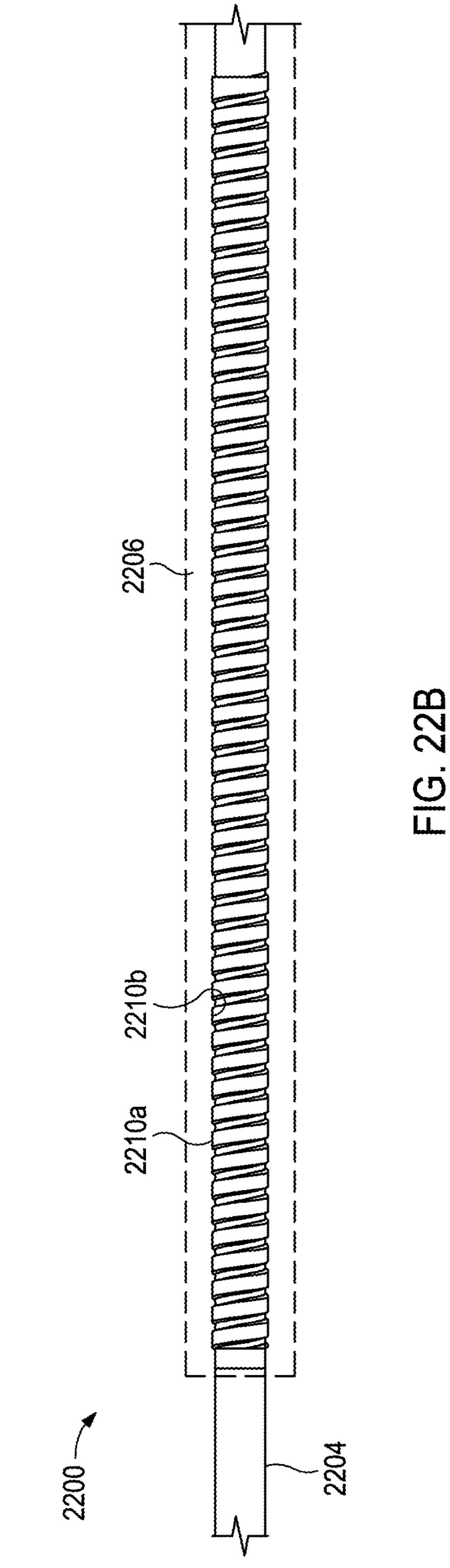
FIG. 22A is an isometric view of an example knife assembly.
FIG. 22B is an enlarged portion of the knife assembly as indicated in FIG. 22A, according to one or more embodiments.

FIG. 22A is an isometric view of an example knife assembly 2200, and FIG. 22B is an enlarged portion of the knife assembly 2200 as indicated by the dashed box included in FIG. 22A, according to one or more embodiments. Referring first to FIG. 22A, the knife assembly 2200 includes a knife 2202, a drive rod 2204, a proximal hypotube 2206, and a push rod 2208.

The knife 2202 may be the same as or similar to any of the knives 1102, 2102 described herein, but could alternatively comprise other types of knives known to those skilled in the art. The knife 2202 may be operatively coupled to the drive rod 2204, which may be the same as or similar to the drive rod 616 described herein. The proximal hypotube 2206 may be operatively coupled to the proximal end of the drive rod 2204, and the push rod 2208 may be operatively coupled to the proximal end of the proximal hypotube 2206. In some embodiments, the push rod 2208 may be the same as or similar to the push rod 708 (FIG. 8).

Referring to FIG. 22B, which is an enlarged view of the knife assembly 2200, as indicated by the dashed box of FIG. 22A, the drive rod 2204 may be operatively coupled to the proximal hypotube 2206 at a threaded engagement. More specifically, the drive rod 2204 may provide and otherwise define external threading 2210*a*, and the proximal hypotube 2206 may provide and otherwise define internal threading 2210*b* sized to receive and threadably mate with the external threading 2210*a*. The knife 2202 and the drive rod 2204 may be separated from the remainder of the knife assembly 2200 by unthreading the drive rod 2204 from the proximal hypotube 2206 at the threaded engagement. This may prove advantageous when it is desired to only replace the knife 2202 and the drive rod 2204 with a new knife and a new drive rod 2204.

In at least one embodiment, it is contemplated herein that the proximal hypotube 2206 may be omitted, and the drive rod 2204 may instead be threadably engaged with the push rod 2208, without departing from the scope of the disclosure.

Figure 23:
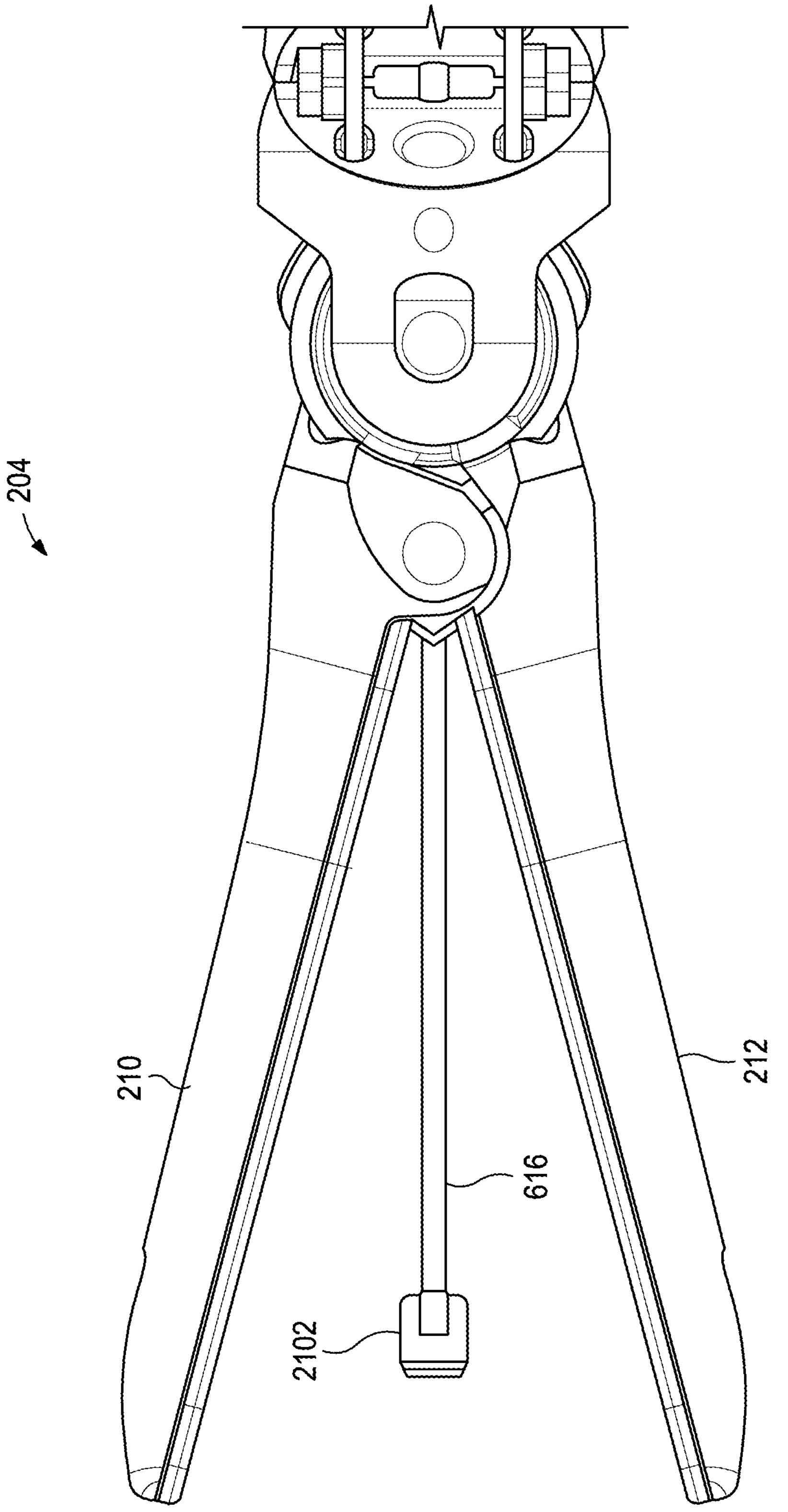
FIG. 23 is an enlarged side view of the end effector, according to one or more embodiments.

FIG. 23 is an enlarged side view of the end effector 204, according to one or more embodiments. As illustrated, the end effector 204 includes the bifurcating jaws 210, 212, which allows the knife 2102 to be exposed when the jaws 210, 212 are in the open position. The knife 2102 shown in FIG. 23 is merely an example and could alternatively be replaced with any of the other knives described herein, without departing from the scope of the disclosure.

In embodiments where it is desired to replace the knife 2102 and/or other portions of the knife assembly, the jaws 210, 212 may be manually opened either at the end effector 204 or by using a manual slider forming part of the drive housing 208 (FIGS. 2 and 4). The drive rod 616 may then be advanced distally to correspondingly advance the knife 2102 out of the end effector 204, and thereby exposing it for removal. In embodiments where the knife 2102 is threaded to the drive rod 616, as described herein, the knife 2102 may be unthreaded (unscrewed) from the drive rod 616, and a new knife may subsequently be threaded onto the distal end of the drive rod 616. The drive rod 616 may then be retracted proximally to correspondingly retract the new knife, and the jaws 210, 212 are closed, thereby completing the replacement process.

In other embodiments, the knife 2102 and the drive rod 616 may be unthreaded from proximal portions of the knife assembly, such as is described above with reference to FIGS. 22A-22B. In such embodiments, the knife 2102 and the interconnected drive rod 616 may be unthreaded from the proximal portions of the jaw assembly 2200, and a new knife and new drive rod may subsequently be threaded back onto the proximal portions of the jaw assembly 2200. The new drive rod may then be retracted proximally to correspondingly retract the new knife, and the jaws 210, 212 may then be closed, thereby completing the replacement process.

Embodiments disclosed herein include:

A. A method of replacing a consumable of a surgical tool includes securing the surgical tool, the surgical tool including a drive housing, an elongate shaft extending distally from the drive housing, an end effector arranged at a distal end of the elongate shaft, and a wrist interposing the distal end of the elongate shaft and the end effector. The method may further include moving the elongate shaft proximally and thereby exposing internal portions of the wrist and the end effector, moving the end effector distally to separate the end effector from the wrist, disconnecting the end effector from proximal portions of the surgical tool, replacing the consumable of the surgical tool, reconnecting the end effector to the proximal portions of the surgical tool, moving the end effector proximally to re-attach the end effector to the wrist, and moving the elongate shaft distally to occlude the internal portions of the wrist and the end effector.

B. A surgical tool configured for a circularity processing system includes a drive housing mountable to the drive housing mount, an elongate shaft extending distally from the drive housing, an end effector arranged at a distal end of the elongate shaft and securable the end effector mount, a wrist interposing the distal end of the elongate shaft and the end effector, and one or more retention clips provided within an interior of the drive housing and engageable with the elongate shaft within the drive housing, wherein removing the one or more retention clips from engagement with the elongate shaft frees the elongate shaft to move proximally into the drive housing and thereby expose internal portions of the wrist and the end effector while the surgical tool is mounted to the disassembly fixture.

C. A method of replacing a consumable of a surgical tool includes securing the surgical tool, the surgical tool including a drive housing, an elongate shaft extending distally from the drive housing, an end effector arranged at a distal end of the elongate shaft, a wrist interposing the distal end of the elongate shaft and the end effector, the wrist including a distal clevis having opposing first and second arms laterally offset from each other and extending distally, each arm defining an open-ended slot that opens distally, and first and second pulleys operatively coupled to the end effector and rotatably mounted to the first and second arms. The method may further include moving the end effector distally and thereby separating the first and second pulleys from the first and second arms by exiting the open-ended slots, disconnecting the end effector from proximal portions of the surgical tool while the wrist remains intact, replacing the consumable of the surgical tool, reconnecting the end effector to the proximal portions of the surgical tool, and moving the end effector proximally to re-attach the end effector to the wrist.

D. A surgical tool configured for a circularity processing system includes a drive housing mountable to the drive housing mount, an elongate shaft extending distally from the drive housing, an end effector arranged at a distal end of the elongate shaft and securable the end effector mount, a wrist interposing the distal end of the elongate shaft and the end effector, and at least one electrical conductor extending from the drive housing and terminating at an electrode mounted to the end effector, the at least one electrical conductor including a spring-tensioned electrical connector including a distal connector attached to a distal length of the at least one electrical conductor, and a proximal connector attached to a proximal length of the at least one electrical conductor.

Each of embodiments A, B, C, and D may have one or more of the following additional elements in any combination: Element 1: wherein one or more retention clips are provided within an interior of the drive housing and engageable with the elongate shaft within the drive housing, and wherein moving the elongate shaft proximally comprises accessing an interior of the drive housing, moving the one or more retention clips out of engagement with the elongate shaft, and moving the elongate shaft proximally and further into the interior of the drive housing. Element 2: wherein the wrist includes a distal clevis having opposing first and second arms laterally offset from each other and extending distally, each arm defining an open-ended slot that opens distally, and the surgical tool further includes first and second pulleys operatively coupled to the end effector and rotatably mounted to the first and second arms, and wherein moving the end effector distally comprises separating the first and second pulleys from the first and second arms by exiting the open-ended slots. Element 3: wherein the surgical tool further includes a drive rod extending to the end effector and terminating at a knife, and wherein disconnecting the end effector from the proximal portions of the surgical tool comprises laterally separating the first and second pulleys from the end effector, disconnecting the drive rod from a push rod extending within the elongate shaft from the drive housing, and moving the end effector and the drive rod distally from the proximal portions of the surgical tool. Element 4: wherein the drive rod is releasably coupled to the push rod via a bayonet connection, and wherein disconnecting the drive rod from the push rod comprises rotating the end effector about a longitudinal axis of the elongate shaft and thereby disconnecting the bayonet connection. Element 5: further comprising disconnecting the end effector from the proximal portions of the surgical tool while the wrist remains intact. Element 6: wherein the surgical tool further includes at least one electrical conductor terminating at an electrode mounted to the end effector, and wherein disconnecting the end effector from the proximal portions of the surgical tool comprises laterally separating the first and second pulleys from the end effector, disconnecting an electrical connector of the at least one electrical conductor from a proximal length of the at least one electrical conductor, and moving the end effector and a distal length of the at least one electrical conductor distally from the proximal portions of the surgical tool. Element 7: wherein the electrical connector comprises a distal connector attached to the distal length of the at least one electrical conductor, and a proximal connector attached to the proximal length of the at least one electrical conductor, and wherein disconnecting the electrical connector comprises detaching the distal and proximal connectors. Element 8: wherein the consumable is the end effector, and where replacing the consumable of the surgical tool comprises replacing the entire end effector. Element 9: wherein a distal linkage is mounted to a proximal end of the end effector, and the end effector includes opposing upper and lower jaws, and wherein disconnecting the end effector from the proximal portions of the surgical tool further comprises detaching a securing band that extends about the distal linkage, separating two or more linkage portions of the distal linkage from the end effector, and separating the upper and lower jaws and thereby exposing a knife secured to a distal end of a drive rod. Element 10: wherein the knife comprises the consumable, and wherein replacing the consumable of the surgical tool comprises replacing the knife. Element 11: wherein the surgical tool further includes at least one electrical conductor terminating at an electrode mounted to a corresponding one of the upper and lower jaws, the electrode comprising the consumable, and wherein replacing the consumable of the surgical tool comprises removing the electrode from the corresponding one of the upper and lower jaws, and attaching a new electrode to the corresponding one of the upper and lower jaws. Element 12: wherein securing the surgical tool comprises mounting the surgical tool to a disassembly fixture, which includes the steps of mounting the drive housing to a drive housing mount of the disassembly fixture, and securing the end effector to an end effector mount of the disassembly fixture.

Element 13: wherein the disassembly fixture includes an elongate base having opposing proximal and distal ends, and wherein the drive housing mount is provided at the proximal end and the end effector mount is provided at the distal end. Element 14: wherein at least one of the one or more retention clips comprises a flexible C-clip. Element 15: wherein the wrist includes a distal clevis having opposing first and second arms laterally offset from each other and extending distally, each arm defining an open-ended slot that opens distally, a distal linkage arranged distal to the distal clevis and mounted to the end effector, and first and second pulleys operatively coupled to the end effector and rotatably mounted to the first and second arms, wherein the first and second pulleys are separable from the first and second arms by moving the end effector distally and thereby allowing the first and second pulleys to exit the open-ended slots. Element 16: wherein the distal linkage includes two or more linkage portions mountable to the end effector, and a securing band extending about the linkage to secure the two or more linkage portions to the end effector, the securing band being detachable to release the two or more linkage portions and thereby allow disassembly of the end effector. Element 17: further comprising at least one electrical conductor extending from the drive housing and terminating at an electrode mounted to the end effector, an electrical connector including a distal connector attached to a distal length of the at least one electrical conductor, and a proximal connector attached to a proximal length of the at least one electrical conductor, and a window defined in a subassembly housed within the elongate shaft and providing physical access to the electrical connector when the elongate shaft is moved proximally. Element 18: wherein the electrical connector comprises a spring-tensioned connector. Element 19: wherein the surgical tool further comprises a push rod extending from the drive housing within the elongate shaft, a drive rod releasably coupled to a distal end of the push rod at a releasable interconnection and extending to the end effector, a knife attached to a distal end of the drive rod, and a shaft sleeve longitudinally translatable within the elongate shaft and retractable to expose the releasable interconnection, wherein uncoupling the releasable interconnection allows the drive rod and the knife to be replaced.

By way of non-limiting example, exemplary combinations applicable to A, B, C, and D include: Element 2 with Element 3; Element 3 with Element 4; Element 3 with Element 5; Element 2 with Element 6; Element 6 with Element 7; Element 9 with Element 10; Element 9 with Element 11; Element 15 with Element 16; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure.

What is claimed is:

1. A method of replacing a consumable of a surgical tool, the method comprising:

moving an elongate shaft of the surgical tool proximally and into an interior of a drive housing of the surgical tool, thereby exposing internal portions of a wrist of the surgical tool and an end effector of the surgical tool;

moving the end effector distally to separate the end effector from the wrist;

disconnecting the end effector from proximal portions of the surgical tool; and replacing the consumable of the surgical tool after disconnecting the end effector.

2. The method of claim 1, wherein one or more retention clips are provided within the interior of the drive housing and engageable with the elongate shaft within the drive housing, and wherein moving the elongate shaft proximally into the interior of the drive housing comprises:

accessing an interior of the drive housing; and moving the one or more retention clips out of engagement with the elongate shaft, thereby allowing the elongate shaft to move proximally into the interior of the drive housing.

3. The method of claim 1, wherein the consumable is the end effector, and where replacing the consumable of the surgical tool comprises replacing the end effector entirely.

4. The method of claim 1, further comprising:

reconnecting the end effector to the proximal portions of the surgical tool;

moving the end effector proximally to re-attach the end effector to the wrist; and moving the elongate shaft distally to occlude the internal portions of the wrist and the end effector.

5. A method of replacing a consumable of a surgical tool, the surgical tool including:

an elongate shaft;

an end effector arranged at a distal end of the elongate shaft; and a wrist interposing the distal end of the elongate shaft and the end effector, wherein the wrist includes a distal clevis having a first arm and an opposing second arm laterally offset from the first arm, each of the first arm and the second arm extending distally and defining an open-ended slot that opens distally, and the surgical tool further includes a first pulley and a second pulley operatively coupled to the end effector and rotatably mounted to the first arm and the second arm, respectively, wherein the method comprises:

moving the elongate shaft proximally and thereby exposing internal portions of the wrist and the end effector;

moving the end effector distally to separate the end effector from the wrist;

disconnecting the end effector from proximal portions of the surgical tool; and replacing the consumable of the surgical tool after disconnecting the end effector, wherein moving the end effector distally comprises separating the first pulley from the first arm and the second pulley from the second arm by exiting the open-ended slots.

6. The method of claim 5, wherein the surgical tool further includes a drive rod extending to the end effector and terminating at a knife, and wherein disconnecting the end effector from the proximal portions of the surgical tool comprises:

laterally separating the first pulley and the second pulley from the end effector;

disconnecting the drive rod from a push rod extending within the elongate shaft from the drive housing; and moving the end effector and the drive rod distally from the proximal portions of the surgical tool.

7. The method of claim 6, wherein the drive rod is releasably coupled to the push rod via a bayonet connection, and wherein disconnecting the drive rod from the push rod comprises rotating the end effector about a longitudinal axis of the elongate shaft and thereby disconnecting the bayonet connection.

8. The method of claim 5, wherein the surgical tool further includes at least one electrical conductor terminating at an electrode mounted to the end effector, and wherein disconnecting the end effector from the proximal portions of the surgical tool comprises:

laterally separating the first pulley and the second pulley from the end effector;

disconnecting an electrical connector of the at least one electrical conductor from a proximal length of the at least one electrical conductor; and moving the end effector and a distal length of the at least one electrical conductor distally from the proximal portions of the surgical tool.

9. The method of claim 8, wherein the at least one electrical connector comprises a distal connector attached to the distal length of the at least one electrical conductor, and a proximal connector attached to the proximal length of the at least one electrical conductor, and wherein disconnecting the electrical connector comprises detaching the distal connector and the proximal connector.

10. A method of replacing a consumable of a surgical tool, the method comprising:

moving an elongate shaft of the surgical tool proximally and thereby exposing internal portions of a wrist of the surgical tool and an end effector of the surgical tool;

moving the end effector distally to separate the end effector from the wrist;

disconnecting the end effector from proximal portions of the surgical tool; and replacing the consumable of the surgical tool after disconnecting the end effector, wherein a distal linkage is mounted to a proximal end of the end effector, and the end effector includes an upper jaw and an opposing lower jaw, and wherein disconnecting the end effector from the proximal portions of the surgical tool comprises:

detaching a securing band that extends about the distal linkage;

separating two or more linkage portions of the distal linkage from the end effector; and separating the upper jaw and the lower jaw and thereby exposing a knife secured to a distal end of a drive rod.

11. The method of claim 10, wherein the knife comprises the consumable, and wherein replacing the consumable of the surgical tool comprises replacing the knife.

12. The method of claim 10, wherein the surgical tool further includes at least one electrical conductor terminating at an electrode mounted to a corresponding one of the upper jaw and the lower jaw, the electrode comprising the consumable, and wherein replacing the consumable of the surgical tool comprises:

removing the electrode from the corresponding one of the upper jaw and the lower jaw; and attaching a new electrode to the corresponding one of the upper jaw and the lower jaw.

13. A method of replacing a consumable of a surgical tool, wherein the method comprises:

moving an elongate shaft of the surgical tool proximally and thereby exposing internal portions of a wrist of the surgical tool and an end effector of the surgical tool;

moving the end effector distally to separate the end effector from the wrist;

disconnecting the end effector from proximal portions of the surgical tool; and replacing the consumable of the surgical tool after disconnecting the end effector, wherein the method further comprises mounting the surgical tool to a disassembly fixture by:

mounting a drive housing of the surgical tool to a drive housing mount of the disassembly fixture; and securing the end effector to an end effector mount of the disassembly fixture.

14. A method of replacing a consumable of a surgical tool, wherein the surgical tool includes a drive housing;

an elongate shaft extending distally from the drive housing;

an end effector arranged at a distal end of the elongate shaft;

a wrist interposing the distal end of the elongate shaft and the end effector, the wrist including a distal clevis having a first arm and an opposing second arm laterally offset from each other and extending distally, each of the first arm and the second arm defining an open-ended slot that opens distally; and a first pulley and a second pulley operatively coupled to the end effector and rotatably mounted to the first arm and the second arm, respectively, wherein the method comprises:

moving the end effector distally causing the first pulley and the second pulley to longitudinally translate out of the open-ended slots and thereby separating the first pulley and the second pulley from the first arm and the second arm, respectively;

disconnecting the end effector from proximal portions of the surgical tool while the wrist remains intact; and replacing the consumable of the surgical tool after disconnecting the end effector from the proximal portions.

15. The method of claim 14, further comprising:

reconnecting the end effector to the proximal portions of the surgical tool; and moving the end effector proximally to re-attach the end effector to the wrist.

16. The method of claim 14, further comprising moving the elongate shaft proximally and into an interior of the drive housing and thereby exposing internal portions of the wrist and the end effector.

* * * * *